United States Patent
Kindig et al.

(10) Patent No.: US 7,335,320 B2
(45) Date of Patent: *Feb. 26, 2008

(54) METHOD FOR THE PRODUCTION OF HYDROGEN-CONTAINING GASEOUS MIXTURES

(75) Inventors: James Kelly Kindig, Phoenix, AZ (US); Thomas E. Weyand, New Brighton, PA (US)

(73) Assignee: Alchemix Corporation, Carefree, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/430,529

(22) Filed: May 8, 2006

(65) Prior Publication Data

US 2007/0060659 A1    Mar. 15, 2007

Related U.S. Application Data

(60) Division of application No. 10/771,163, filed on Feb. 3, 2004, now abandoned, which is a continuation of application No. 10/178,889, filed on Jun. 24, 2002, now Pat. No. 6,685,754, which is a continuation-in-part of application No. 10/085,436, filed on Feb. 28, 2002, now Pat. No. 6,663,681, which is a continuation-in-part of application No. 09/800,769, filed on Mar. 6, 2001, now Pat. No. 6,682,714, and a continuation-in-part of application No. 09/800,423, filed on Mar. 6, 2001, now abandoned, and a continuation-in-part of application No. 09/800,421, filed on Mar. 6, 2001, now Pat. No. 7,232,472, and a continuation-in-part of application No. 09/800,434, filed on Mar. 6, 2001, now Pat. No. 6,620,398.

(51) Int. Cl.
*C01B 3/10* (2006.01)
*C01B 31/18* (2006.01)

(52) U.S. Cl. .................. 252/373; 423/418.2; 423/657; 423/658

(58) Field of Classification Search ................ 423/657, 423/658, 418.2; 252/373
See application file for complete search history.

(56) References Cited

U.S. PATENT DOCUMENTS

| | | | |
|---|---|---|---|
| 107,809 A | 9/1870 | Pond et al. |
| 1,592,861 A | 7/1926 | Leonarz |
| 2,953,445 A | 9/1960 | Rummel |
| 3,526,478 A | 9/1970 | Pelczarski et al. |
| 4,187,672 A | 2/1980 | Rasor |
| 4,310,503 A * | 1/1982 | Erickson ................... 423/657 |
| 4,388,084 A | 6/1983 | Okane et al. |
| 4,406,666 A | 9/1983 | Paschen et al. |
| 4,459,137 A | 7/1984 | Tanoue et al. |
| 4,496,369 A | 1/1985 | Törneman |
| 4,511,372 A | 4/1985 | Axelsson |
| 4,565,551 A | 1/1986 | Okane et al. |

(Continued)

*Primary Examiner*—Wayne A. Langel
(74) *Attorney, Agent, or Firm*—Marsh Fischmann & Breyfogle LLP

(57) ABSTRACT

A method for the production of a hydrogen-containing gas composition, such as a synthesis gas including hydrogen and carbon monoxide. The molar ratio of hydrogen to carbon monoxide ($H_2$:CO) in the synthesis gas can be well-controlled to yield a ratio that is adequate for the synthesis of useful products such as methane or methanol, without the need to remove carbon oxides from the gas stream to adjust the ratio.

18 Claims, 8 Drawing Sheets

U.S. PATENT DOCUMENTS

| | | |
|---|---|---|
| 5,395,405 A | 3/1995 | Nagel et al. |
| 5,435,814 A | 7/1995 | Miller et al. |
| 6,620,398 B2 * | 9/2003 | Kindig et al. ............... 423/359 |
| 6,663,681 B2 * | 12/2003 | Kindig et al. ............... 48/127.5 |
| 6,682,714 B2 * | 1/2004 | Kindig et al. ............... 423/657 |
| 6,685,754 B2 * | 2/2004 | Kindig et al. ................. 48/210 |

* cited by examiner

METHOD FOR THE PRODUCTION OF HYDROGEN-CONTAINING GASEOUS MIXTURES

CROSS-REFERENCE TO RELATED APPLICATIONS

This application is a divisional of U.S. patent application Ser. No. 10/771,163, filed on Feb. 3, 2004, abandoned, which is a continuation application of U.S. patent application Ser. No. 10/178,889, filed on Jun. 24, 2002, now U.S. Pat. No. 6,685,754, which is continuation-in-part of U.S. patent application Ser. No. 10/085,436, filed on Feb. 28, 2002, now U.S. Pat. No. 6,663,681, which is a continuation-in-part of U.S. patent application Ser. No. 09/800,769. filed Mar. 6, 2001, now U.S. Pat. No. 6,682,714, U.S. patent application Ser. No. 09/800,423 filed Mar. 6, 2001, now abandoned, U.S. patent application Ser. No. 09/800,421 filed Mar. 6, 2001 now U.S. Pat. No. 7,232,472 and U.S. patent application Ser. No. 09/800,434 filed Mar. 6, 2001, now U.S. Pat. No. 6,620,398. Each of the foregoing is incorporated herein by reference in their entirety.

STATEMENT REGARDING FEDERALLY FUNDED RESEARCH

None

BACKGROUND OF THE INVENTION

1. Field of the Invention

The present invention is directed to a method for the production of valuable hydrocarbon products by reacting a carbonaceous material and steam in a molten metal to form a synthesis gas that can be used to produce high-value hydrocarbon products. More particularly, the present invention is directed to a method for the production of a synthesis gas that includes a controlled ratio of hydrogen to carbon monoxide by contacting a carbonaceous material and a reactive metal with steam, wherein a portion of the steam reacts with the carbonaceous material and a portion of the steam reacts with the reactive metal. The synthesis gas can be used to form high-value hydrocarbon products, such as methane or methanol.

2. Description of Related Art

Recently, the United States and other countries have experienced a shortage of natural gas and as a result, natural gas prices for consumers have increased substantially. Accordingly, there is a pressing need for economic methods for the manufacture of a high-value heating gas that can be used in place of natural gas. Natural gas has a composition that includes from about 80 percent to 93 percent methane ($CH_4$), the balance including ethane ($C_2H_6$), propane ($C_3H_8$), butane ($C_4H_{10}$) and nitrogen ($N_2$). Methane, the primary component of natural gas, has a heating value of about 21,520 Btu/lb. Thus, an economic method for the production of methane would supplement the use of non-renewable natural gas.

There are many natural resources in addition to natural gas that are utilized to produce energy. For example, coal can be burned in conventional boilers to generate steam, which is converted to energy through steam turbines. 85 percent of the electricity in the United States is generated by combusting fossil fuels, namely coal, oil and natural gas. Coal however, because of its high carbon content, generates large quantities of carbon dioxide ($CO_2$), and the use of coal for electricity generation is a major contributor to the 5.5 billion tons of $CO_2$ emitted by the United States per annum. The 5.5 billon tons of $CO_2$ amounts to one-fourth of the world emissions. Coal combustion is also responsible for other pollution, most notably sulfur dioxide ($SO_2$) and nitrogen oxides ($NO_x$), both of which are now regulated.

Furthermore, only 30 percent of the heat generated by burning coal is converted into electricity and 70 percent is wasted to the atmosphere. In contrast, electrical generation in modern plants burning natural gas is about 50 percent efficient and natural gas produces only about 60 percent of the $CO_2$ that coal produces.

As an alternative to simply burning high carbon containing materials, such as coal, the materials can be converted to a synthesis gas in a gasifier. Synthesis gas includes five major gaseous components—carbon monoxide (CO), hydrogen ($H_2$), methane, carbon dioxide and steam ($H_2O$). These gases are derived from the carbon (C), hydrogen, and oxygen ($O_2$) molecules found in the high carbon containing material and steam used to convert the high carbon containing material to synthesis gas. Other elements, designated impurities, typically found with carbonaceous materials include sulfur (S), nitrogen ($N_2$), chlorine ($Cl_2$) and fluorine (F). These impurities can form minor amounts of other gaseous species. Taken together the major and minor gases constitute a "raw" synthesis gas stream. As used herein, synthesis gas refers to the gas mixture after the minor gases have been removed. Nitrogen, steam and carbon dioxide do not contribute to the heating value and therefore typically are reduced or eliminated from the gas stream. The term "syngas" refers to a gaseous mixture that includes only hydrogen and carbon monoxide.

Synthesis gas has numerous applications, including the conversion of the synthesis gas into valuable hydrocarbons. In one application, the synthesis gas can be converted to methane, which is burned in a combined cycle power plant to generate electricity. The combined cycle gas turbines can be located at coal-fired generating stations thereby taking advantage of existing coal-handling infrastructure and electrical transmission lines. Most importantly, compared to coal-fired electrical generators, the conversion efficiency of thermal to electrical energy increases by about 67 percent. Concomitantly, there is a reduction in carbon dioxide emissions per unit of electricity.

For a gas turbine, gas is input to the turbine and the output is thermal energy. For increased efficiency, a gas with a high thermal energy per cubic foot is desirable. The net heating value (heat of combustion) of the three major components of synthesis gas are illustrated in Table 1 below. These values assume that the heat contained in the steam, the combustion product of hydrogen, is not recovered.

TABLE 1

Net Heats of Combustion

| Synthesis Gas Component | Btu/lbs | Btu/ft$^3$ |
| --- | --- | --- |
| Carbon Monoxide | 4,347 | 322 |
| Hydrogen | 51,623 | 275 |
| Methane | 21,520 | 913 |

As is illustrated in Table 1, methane releases more than three times the amount of heat that hydrogen releases on a per cubic foot basis. The reason for this is that hydrogen occupies more cubic feet on a per pound basis, even though hydrogen has more Btu on a per pound basis. Due to its clean burning nature and high heat content, methane is the preferred fuel. Consequently, syngas ($H_2$ and CO) is more economically burned after it is converted to methane.

Syngas can be used to form other hydrocarbons in addition to methane. Since 1955, SASOL, a South African entity has been producing a waxy synthetic crude from syngas. Some transportation fuel, about 11 percent gasoline, is extracted from the synthetic crude. However, due to the large portion of hydrocarbons having a high molecular weight and oxygenated organics that are also produced, other approaches have been investigated for making specific materials from syngas.

There are well known processes for producing methanol ($CH_3OH$) and acetic acid ($CH_3COOH$) from syngas, for example. Typically, methanol is produced using syngas derived from natural gas, which exerts further pressure on the price and availability of natural gas. At least one major US oil company has developed a family of catalysts that produce a mixture of hydrocarbons in the gasoline range with high selectivity from methanol. Because methanol can be readily made from syngas, and catalysts are available for converting methanol into gasoline with great selectivity, coal-derived syngas affords the US an opportunity to achieve energy independence.

Methanol is also a chemical building block for manufacturing a wide array of other products, including: MTBE (methyl tertiary butyl ether) used in reformulated gasoline; formaldehyde resins, used in engineered wood products and products such as seat cushions and spandex fibers; acetic acid used to make PET (polyethylene terepthalate) plastic bottles and polyester fibers; and windshield wiper fluid. Additionally, methanol is relatively environmentally benign, is less volatile than gasoline and is a leading candidate to power fuel cell vehicles.

There are known processes for converting coal into gaseous products. Hydrogasification converts coal and steam into a raw synthesis gas. Gasification, a companion process, employs coal, steam and oxygen and produces hydrogen, carbon monoxide and carbon dioxide, but no methane. Pyrolysis, which utilizes heat alone, partitions coal into volatile matter and a coke or char. The volatile matter includes hydrogen, oxygen, some portion of the carbon (volatile carbon), organic sulfur and trace elements. The coke or char includes the balance of the (fixed) carbon and the ash derived from the mineral matter accompanying the organics.

Heat by itself disproportionates gaseous volatile matter, derived from coal, into methane and carbon as is illustrated by Equation 1.

$$CH_x \rightarrow (x/4) CH_4 + [1-(x/4)]C \quad (1)$$

(where the value of x must be less than 4)

The hydropyrolysis reaction combines hydrogen and volatile matter to form methane and carbon. This reaction, illustrated by Equation 2, is exothermic.

$$CH_x + m H_2 \rightarrow [(x+2m)/4]CH_4 + \{1-[(x+2m)/4]\}C \quad (2)$$

(where the sum of x plus 2m must be less than 4)

The following solid-gas chemical reactions are applicable to the hydrogasification of organics at temperatures above 1200° C. The highly exothermic reaction of carbon and oxygen illustrated by Equation 3 can be a primary source of process heat, producing about −394 MJ/kg-mole of heat.

$$2 C + O_2 \rightarrow 2 CO \quad (3)$$

The hydrogasification of carbon is also an exothermic reaction, illustrated by Equation 4, yielding −75 MJ/kg-mole of heat.

$$C + 2 H_2 \rightarrow CH_4 \quad (4)$$

The steam-carbon reaction illustrated by Equation 5, is highly endothermic, requiring +175 MJ/kg-mole of heat.

$$C + H_2O \rightarrow CO + H_2 \quad (5)$$

Gas phase reactions, applicable to the formed fuel gases at temperatures below 1000° C. include the mildly exothermic (2.8 MJ/kg-mole) water gas shift reaction, illustrated in Equation 6.

$$CO + H_2O \rightarrow H_2 + CO_2 \quad (6)$$

The highly exothermic methanation reaction is illustrated in Equation 7 (−250 MJ/kg-mole).

$$CO + 3 H_2 \rightarrow CH_4 + H_2O \quad (7)$$

Gasification is the process step that converts a solid (or liquid) fuel into a gaseous fuel by breaking (disassembling) the fuel into its constituent parts (molecules). When gasified with steam and oxygen, organic material is converted into a synthesis gas that may include five gaseous components: carbon monoxide, hydrogen, methane, carbon dioxide and steam.

The concentration of the individual product gases (all reactions above) all move in the direction of thermodynamic equilibrium, limited by kinetics, which is strongly related to temperature. The temperature of the gasifier, therefore, is the predominate factor that determines which gaseous species will form and in what amount. FIG. 1 illustrates the influence of temperature on a mixture of gases (four parts hydrogen and one part each carbon monoxide and methane) allowed to come to thermodynamic equilibrium. This mixture was thermodynamically equilibrated at various temperatures, over a range from 200° C. to 1200° C. In addition to temperature, the type of gasifying equipment (moving bed, fluidized bed or entrained flow) also exerts a strong influence on the resulting synthesis gas mix.

Equation 8 illustrates the ideal coal hydrogasification reaction.

$$Coal + H_2O \rightarrow CH_4 + CO_2 \quad (8)$$

The ideal hydrogasification reaction illustrated by Equation 8 is slightly endothermic and is favorable for methane production only at low temperatures, where the kinetics are too slow to be commercially useful. To circumvent this thermodynamic dilemma, various hydrogasification processes have been proposed for coal. These processes conduct a sequence of related chemical reactions such that the sum of the reactions is identical to the ideal reaction of Equation 8. One sequence of reactions includes gasification to convert the solid fuel, coal or other organic material, into a gaseous fuel by reacting it with steam and usually oxygen at high temperatures and in an entrained flow gasifier. This gasification step produces a gas comprised predominantly of hydrogen and carbon monoxide, with some impurities. Typically, the resulting ratio of hydrogen to carbon monoxide ($H_2$:CO) for entrained flow reactors falls between 0.5 and 0.8. The water gas shift reaction can be used to increase the ratio of hydrogen to carbon monoxide by subtracting carbon monoxide from the system. This is done by reacting carbon monoxide with additional steam to produce carbon dioxide. Sulfur and other impurities can also be removed from the raw synthesis gas. The resulting carbon dioxide can be removed by pressure swing adsorption or amine scrubbing. Finally, the scrubbed syngas, with the proper $H_2$:CO ratio, is passed over appropriate catalysts to produce, for example, methane (3:1 ratio) or methanol (2:1 ratio).

The H$_2$:CO ratio produced by other gasifying systems varies, as shown below in Table 2. (Data taken from Perry's Chemical Engineers' Handbook, 7$^{th}$ ed, 1997, Table 27-11)

TABLE 2

Gasifying Systems

| COMMERCIAL GASIFYING SYSTEM | | H$_2$:CO RATIO |
|---|---|---|
| Moving Bed Type | Lurgi | 1.77 |
| | BG Lurgi | 0.58 |
| Fluid Bed Type | KRW (Air) | 0.63 |
| | KRW (Oxygen) | 0.51 |
| Entrained Flow | Shell | 0.42 |
| | Texaco | 0.77 |

The H$_2$:CO ratio for the above gasifiers is less than 1.9. The Lurgi gasifying process has the highest H$_2$ to CO ratio, however, it can only utilize coal in the size range of 2 mm to 50 mm. The resulting requirement for disposal of material smaller than 2 mm imposes an onerous economic burden on the Lurgi process. An example of a gasifier having a rotatable grate is disclosed in U.S. Pat. No. 3,930,811, by Hiller et al. The H$_2$:CO ratios for all other gasifiers listed in Table 2 is less than 1. These ratios are established primarily by the reactor type and the type of coal. This fixed ratio, unique to each gasifier-coal combination, occurs because all of the gasifiers above use oxygen to supply adequate input heat to secure a process heat balance for a specified coal and steam rate. Any change in coal rate or steam rate, for the intended purpose of affecting the H$_2$:CO ratio, would destroy the heat balance. Prabhakar G. Bhandarkar in an article entitled Gasification Overview Focus on India, Hydrocarbon Asia, November/December 2001, discusses various gasification systems including some of those listed in Table 2.

Molten metal gasification is one technique for gasifying coal. An example of a molten metal gasification process is disclosed in U.S. Pat. No. 4,389,246 by Okamura et al. issued Jun. 21, 1983 and assigned to Sumitomo Metal Industries. Okamura et al. discloses an example (Example 1) wherein coal and steam was fed into a furnace containing molten iron at 1500° C. The coal was fed at a rate of 3.5 tons per hour and the steam was fed at a rate of 400 kg/hr (0.44 tons/hr). The steam and coal were blown onto the surface of the molten metal along with oxygen at high velocities to produce a depression of a specified geometry. The average gas production was 7500 Nm$^3$/hr. The actual composition of the gas as reported by Okamura et al. was:

| Carbon Monoxide | 62.5% |
|---|---|
| Hydrogen | 33.9% |
| Oxygen | 0.02% |
| Nitrogen | 1.4% |
| Carbon Dioxide | 2.0% |
| Total Sulfur | <80 ppm |

The Okamura et al. example is typical of oxygen-blown slagging gasifiers. The critical parameter from the example is the H$_2$:CO ratio, which is only 0.54:1 (33.9/62.5). In contrast, a 3:1 or 2:1 ratio is necessary to produce methane or methanol, respectively.

In addition to the Okamura et. al. patent there are other known processes for producing synthesis gas from steam and carbon. For example, U.S. Pat. No. 1,592,861 by Leonarz discloses a method for the production of water gas (primarily H$_2$ and CO) by contacting steam with uncombined carbon in a bath of molten metal. The steam is dissociated into its constituent elements by carburetion at temperatures of 900° C. to 1200° C. The carbon combined with the oxygen of the gas is sufficient in quantity to produce carbon monoxide but not to make an appreciable quantity of carbon dioxide.

U.S. Pat. No. 2,953,445 by Rummel discloses the gasification of fuels and decomposition of gases in a molten slag bath. It is disclosed that a water gas composition is obtained composed primarily of hydrogen and carbon monoxide wherein the ratio of hydrogen to carbon monoxide is about 0.38:1.

U.S. Pat. No. 4,187,672 by Rasor discloses an apparatus for converting carbonaceous material into fuel gases. For example, raw coal can be gasified in a molten metal bath such as molten iron at temperatures of 1200° C. to 1700° C. Steam is injected to react with the carbon endothermically and moderate the reaction.

U.S. Pat. No. 4,388,084 by Okane et al. discloses a process for the gasification of coal by injecting coal, oxygen and steam onto molten iron at a temperature of about 1500° C. A gas product is produced having a ratio of hydrogen to carbon monoxide of about 0.5:1.

U.S. Pat. No. 5,645,615 by Malone et al. discloses a method for decomposing carbon and hydrogen containing feeds, such as coal, by injecting the feed into a molten metal using a submerged lance.

Donald B. Anthony, in a 1974 Thesis entitled "Rapid Devolatilization and Hydrogasification of Pulverized Coal," found that rapid heating of coal in the presence of hydrogen can increase the amount of volatile matter significantly. Under thermal decomposition, different chemical bonds rupture at different temperatures. The rupturing bonds release volatiles and initiate char-forming reactions. Short-lived (<1 second) intermediaries in the char-forming sequence can react with hydrogen to form additional volatile matter. It was also found that freshly devolatilized coal is more reactive than pretreated coal. Further, the carbon that is residual from freshly devolatilized coal may possess excess free energies. The equilibrium constant for the hydrogasification reaction may be larger by a factor of 10 or more.

A significant limitation of the foregoing methods for producing syngas is that the synthesis gas must be treated to remove carbon oxides before the gas product can be used to produce high-value products such as methane or methanol. Process steps to eliminate carbon oxides from the gas stream are relatively costly. It would be advantageous to provide a method that can provide a synthesis gas having a controlled ratio of hydrogen to carbon monoxide, and in particular where the molar ratio of hydrogen to carbon monoxide is at least about 1:1, such as at least about 2:1, for the subsequent formation of high-value hydrocarbons.

BRIEF SUMMARY OF THE INVENTION

According to one embodiment, the present invention provides a method for the conversion of a carbonaceous material, such as coal, into a valuable synthesis gas that can be converted to high-value hydrocarbons such as methane or methanol. The ratio of hydrogen to carbon monoxide in the synthesis gas can be well controlled to enable the economical production of hydrocarbons, such as methane or methanol.

The present invention allows coal, an abundant resource, to be converted to synthesis gas, which is then available for conversion to clean burning methane and methanol, thereby relieving demand on the natural gas supply and reducing $CO_2$ emissions. Also, synthesis gas from coal according to the present invention can serve as the basic component from which synthetic gasoline can be manufactured.

According to one embodiment of the present invention, a method is provided for the production of a gas stream including hydrogen and carbon monoxide wherein the molar $H_2$:CO ratio is at least about 1:1. The method includes the steps of providing a molten metal in a reactor that includes at least a first reactive metal, contacting steam with the reactive metal to react a first portion of the steam with the reactive metal and form hydrogen gas and a metal oxide and contacting a carbonaceous material with the molten metal in the presence of steam to react the carbonaceous material with a second portion of the steam and form carbon monoxide gas. A gas stream can be extracted from the reactor which has a molar $H_2$:CO ratio of at least about 1:1, such as at least about 2:1.

According to another embodiment of the present invention, a method for the production of a gas stream including hydrogen and carbon monoxide is provided wherein the $H_2$:CO molar ratio is at least about 1:1. The method includes providing a molten metal in a reactor including at least a first reactive metal, contacting steam with the molten metal to react a first portion of the steam with the reactive metal to form hydrogen gas and a metal oxide, contacting a carbonaceous material with the molten metal to react the carbonaceous material with a second portion of the steam and form carbon monoxide, extracting a gas stream from the reactor having a molar $H_2$:CO ratio of at least about 1:1. After a period of time, the steam flow is terminated and the metal oxide is reduced with a reductant back to the metal. By operating two such reactors in parallel, a gas stream containing $H_2$ and CO can be produced substantially continuously.

According to another embodiment of the present invention, a method for the gasification of coal is provided. The method includes the steps of injecting coal into a molten metal contained a reactor, injecting steam into the molten metal and extracting a gas stream from the reactor including hydrogen and carbon monoxide wherein the molar ratio of $H_2$:CO is at least about 1:1. A sufficient excess of steam is injected into the molten metal to react the first portion of the steam with the coal and form carbon monoxide and to react a second portion of the steam with the molten metal to produce hydrogen gas and a metal oxide.

The present invention is also directed to a method for the production of hydrocarbon products. According to one embodiment, a method for the production of methane gas is provided. The method includes the steps of providing a molten metal including at least a first reactive metal in a reactor, injecting steam into the molten metal to react a first portion of the steam with the reactive metal to form hydrogen gas and a metal oxide, injecting a carbonaceous material into the molten metal to react the carbonaceous material with a second portion of the steam and form carbon monoxide, extracting a gas stream from the reactor including hydrogen and carbon monoxide and reacting the gas stream in the presence of a catalyst to form methane gas. The methane gas can then be burned to produce electricity, such as in a combined cycle generator.

According to another embodiment of the present invention, a method for the production of methanol is provided. The method includes the steps of providing a molten metal having at least a first reactive metal in a reactor, injecting steam into the molten metal to react a first portion of the steam with the reactive metal to form hydrogen gas and a metal oxide, injecting a carbonaceous material into the molten metal to react the carbonaceous material with a second portion of the steam and form carbon monoxide, extracting a gas stream from the reactor including hydrogen and carbon monoxide, and reacting the gas stream in the presence of a catalyst to form methanol.

According to another embodiment of the present invention, a method for the production of ammonia is provided. The method includes contacting steam with the reactive metal in a reactor to reduce at least a portion of the steam and form hydrogen gas, contacting air with the reactive metal to combust oxygen contained in the air and form a nitrogen gas stream, and extracting a gas stream from the reactor comprising hydrogen gas and nitrogen gas. The hydrogen gas and nitrogen gas can then be reacted in the presence of a catalyst to form ammonia.

According to another embodiment of the present invention, a method for the formation of a gas stream including hydrogen and at least a second gaseous component is provided. The method includes contacting steam with a reactive metal in a reactor to oxidize the reactive metal and form hydrogen gas. At least a second material is contacted with at least one of the steam and the reactive metal in the reactor to form a second gaseous component. A gas stream is then extracted from the reactor that includes hydrogen gas and the second gaseous component. The second gaseous component can be, for example, a carbon compound or a nitrogen compound.

DETAILED DESCRIPTION OF THE INVENTION

Figure 1:
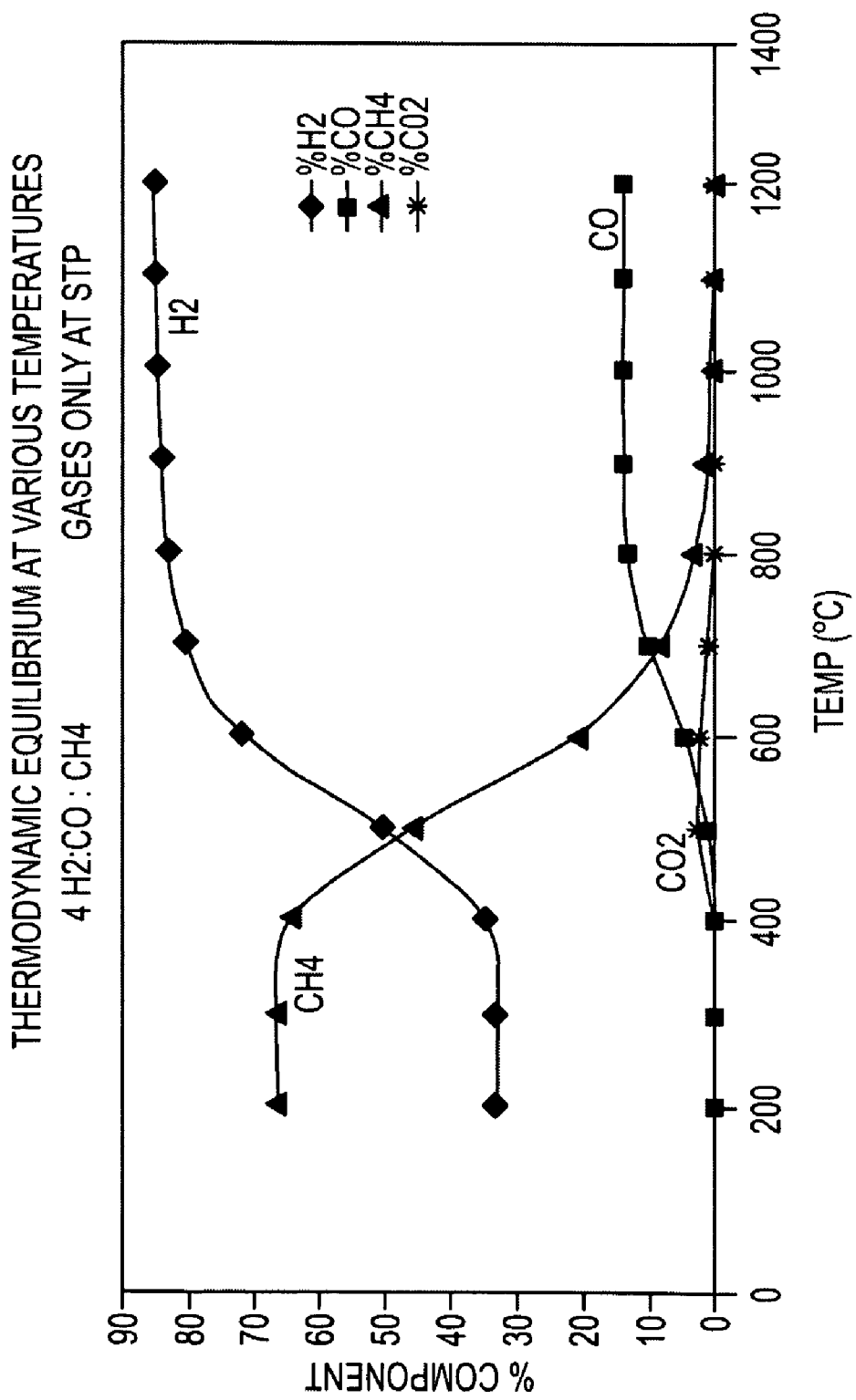
FIG. 1 illustrates the thermodynamic equilibrium of hydrogen, carbon dioxide and methane at various temperatures.

According to the present invention, steam is contacted with both a reactive metal and a second material within a reactor to form a gas composition that includes at least hydrogen and a second gaseous component. In one embodiment, the second material is a carbonaceous material and the second gaseous component is carbon monoxide. Oxygen contained in a first portion of the steam preferentially reacts with the reactive metal to oxidize the reactive metal to a metal oxide and reduce the first portion of the steam to form a hydrogen-containing gas. A second portion of the steam reacts with the carbonaceous material to form carbon monoxide and hydrogen. In one embodiment, production of the synthesis gas continues until the concentration of the reactive metal in the reactor is reduced to a minimum concentration that is dictated by economics, at which point the injection of the steam is terminated. Then, a reductant is introduced into the reactor to reduce the metal oxide back to the reactive metal. By switching between a flow of steam and carbonaceous material and a flow of reductant between two or more reactors, synthesis gas can be produced substantially continuously.

According to the present invention, syngas can be produced and extracted from the reactor having a controlled ratio of hydrogen to carbon monoxide. Advantageously, the syngas can have a higher ratio of hydrogen to carbon monoxide than synthesis gas produced in the prior art, particularly by the gasification of coal, and does not require the removal of carbon oxides from the synthesis gas to produce a syngas with the appropriate $H_2$ to CO ratio prior to forming high-value hydrocarbons such as methane and methanol. In addition, the synthesis gas can have a relatively low concentration of carbon dioxide.

According to the present invention, at least a portion of the steam is contacted with a reactive metal, preferably a molten metal, disposed in a reactor. The reactive metal is reactive with steam to form hydrogen gas and a metal oxide in accordance with Equation 9.

$$xMe + yH_2O \rightarrow yH_2 + Me_xO_y \tag{9}$$

The reactive metal preferably has an oxygen affinity that is similar to the oxygen affinity of hydrogen and reacts with the steam to form the metal oxide. For example, the reactive metal can be selected from the following metals or their alloys: germanium (Ge), iron (Fe), zinc (Zn), tungsten (W), molybdenum (Mo), indium (In), tin (Sn), cobalt (Co) and antimony (Sb). A particularly preferred reactive metal according to the present invention is iron and according to one embodiment the reactive metal is molten iron.

According to one preferred embodiment, the reactive metal is at least partially dissolved within a second metal or mixture of metals. The metal into which the reactive metal is dissolved is referred to herein as the diluent metal. The diluent metal may also be reactive with steam, in which case it can be selected from the group of reactive metals disclosed hereinabove, provided that the diluent metal is less reactive than the reactive metal. Alternatively, the diluent metal may be selected from the metals wherein the oxygen partial pressure ($pO_2$) in equilibrium with the metal and oxides together is relatively high. These include nickel (Ni), copper (Cu), ruthenium (Ru), rhodium (Rh), palladium (Pd), silver (Ag), cadmium (Cd), rhenium (Re), osmium (Os), iridium (Ir), platinum (Pt), gold (Au), mercury (Hg), lead (Pb), bismuth (Bi), selenium (Se) and tellurium (Te). More than one diluent metal can be utilized in the molten metal mixture. The diluent metal should not be a metal wherein the oxygen partial pressure in equilibrium with metal and metal oxide together is extremely low.

Preferably, the diluent metal should: (1) combine with the reactive metal to be liquid in the temperature range of about 400° C. to 1600° C.; (2) have a very low vapor pressure over this temperature range; and (3) have the capacity to hold the reactive metal in solution. According to a preferred embodiment of the present invention, the diluent metal is tin and in one embodiment, the diluent metal consists essentially of tin. However, the molten metal mixture can also include additional diluent metals, particularly copper and nickel.

A particularly preferred molten metal mixture for steam reduction to form hydrogen according to the present invention includes iron as the reactive metal and tin as the diluent metal. Iron has a high solubility in molten tin at elevated temperatures and the melting temperature of the mixture is substantially lower than the melting temperature of pure iron (1538° C.). Although tin is also reactive with steam, it is less reactive than iron. The tin-iron system is disclosed in detail in co-pending U.S. patent application Ser. No. 10/085,436 entitled "Method for the Production of Hydrogen and Applications Thereof" which is incorporated herein by reference in its entirety.

Due to thermodynamics, steam reduction reactions to form hydrogen gas from a metal require an excess of steam well above the stoichiometric requirement. This excess of steam according to the present invention enables the formation of hydrogen gas and thereby increases the ratio of hydrogen to carbon monoxide in the synthesis gas extracted from the reactor.

The total steam requirement for hydrogen production (the mass ratio of steam required to hydrogen produced) using iron is much less than for tin at all temperatures. Additionally, iron will preferentially oxidize in the molten metal mixture. While not wishing to be bound by any theory, it is believed that some reactive tin is oxidized to tin oxide, but is immediately reduced back to tin:

$$2H_2O + Sn \rightarrow SnO_2 + 2H_2 \tag{10}$$

$$SnO_2 + 2Fe \rightarrow 2FeO + Sn \tag{11}$$

$$\text{Net:} \quad 2H_2O + Fe \rightarrow FeO + 2H_2 \tag{12}$$

The thermodynamic steam requirement for tin at 660° C. is approximately equal to the thermodynamic steam requirement for iron at 1200° C. However, the production of hydrogen using tin as a reactive metal at 660° C. is not practical since the kinetics (i.e., the reaction rate) are very poor and therefore very long residence times (i.e., the time that the steam is in contact with the tin) are required.

At 1200° C., the kinetics for both tin and iron are excellent. The steam requirement for tin, however, is much greater than for iron. The residence time that the steam is in contact with the reactive metal is increased by the use of a diluent metal. For purposes of illustration, a comparison of the thermodynamic steam requirement and the nominal residence times at a temperature of 1200° C. and various pressures for dissolved iron (50 wt. % iron in tin) compared to pure tin is illustrated in Tables 3 and 4. Table 3 illustrates the total steam required to produce one ton of hydrogen at 1200° C.

TABLE 3

Steam Requirement for Hydrogen Production

| System | $pH_2/pH_2O$ | Stoichiometric Steam (tons) | Thermodynamic Steam (tons) | Total Steam (tons) |
|---|---|---|---|---|
| Pure Tin | 0.118 | 8.94 | 76.01 | 84.94 |
| Tin/Iron (50:50 by weight) | 1.732 | 8.94 | 12.21 | 21.15 |

Table 4 illustrates the nominal residence times of the steam at a production rate of 4.439 tons of hydrogen per hour.

TABLE 4

Nominal Steam Residence Time

| System | Total Steam (m³/hr) | Melt Volume (m³) | Nominal Residence Time (seconds) | | |
|---|---|---|---|---|---|
| | | | 1 atm. | 5 atm. | 10 atm. |
| Pure Tin | 2.51 × 10⁶ | 17.93 | 0.026 | 0.13 | 0.26 |
| Tin/Iron (50:50 by weight) | 0.625 × 10⁶ | 24.41 | 0.141 | 0.70 | 1.41 |

It is evident from the data in Tables 3 and 4 that pure tin systems require substantially more steam to produce hydrogen than the dissolved iron systems in accordance with the present invention. Table 4 also shows that the nominal residence time available for tin to react with the steam is considerably less than the nominal residence time available for iron dissolved in tin to react with the steam. Nominal or apparent residence time is the time available for the steam (reactant of the process) to traverse the space occupied by the quantity of reactive metal employed. In Table 4, the melt volume is the quantity of metal required by stoichiometry at the hydrogen production rate of 4.439 tons of hydrogen per hour. During this time, ideally, hydrogen will be produced in an amount corresponding to the thermodynamic $pH_2/pH_2O$ ratio. An amount of reactive metal greater than the stoichiometric amount may be used to increase nominal residence time, but the consequence is increased reactor size and cost. Increased pressure also increases the reaction time available between the steam and the reactive metal, however, this also adds to cost.

Thus, one advantage of utilizing a reactive metal dissolved in a diluent metal in accordance with the present invention is that the residence time of the steam within the reactor is increased with respect to the mass of the reactive metal. That is, a given mass of iron will occupy a first volume as pure iron, but the same mass of iron will be distributed over about twice the volume if the iron is in a 50 weight percent mixture with a diluent metal such as tin.

Figure 2:
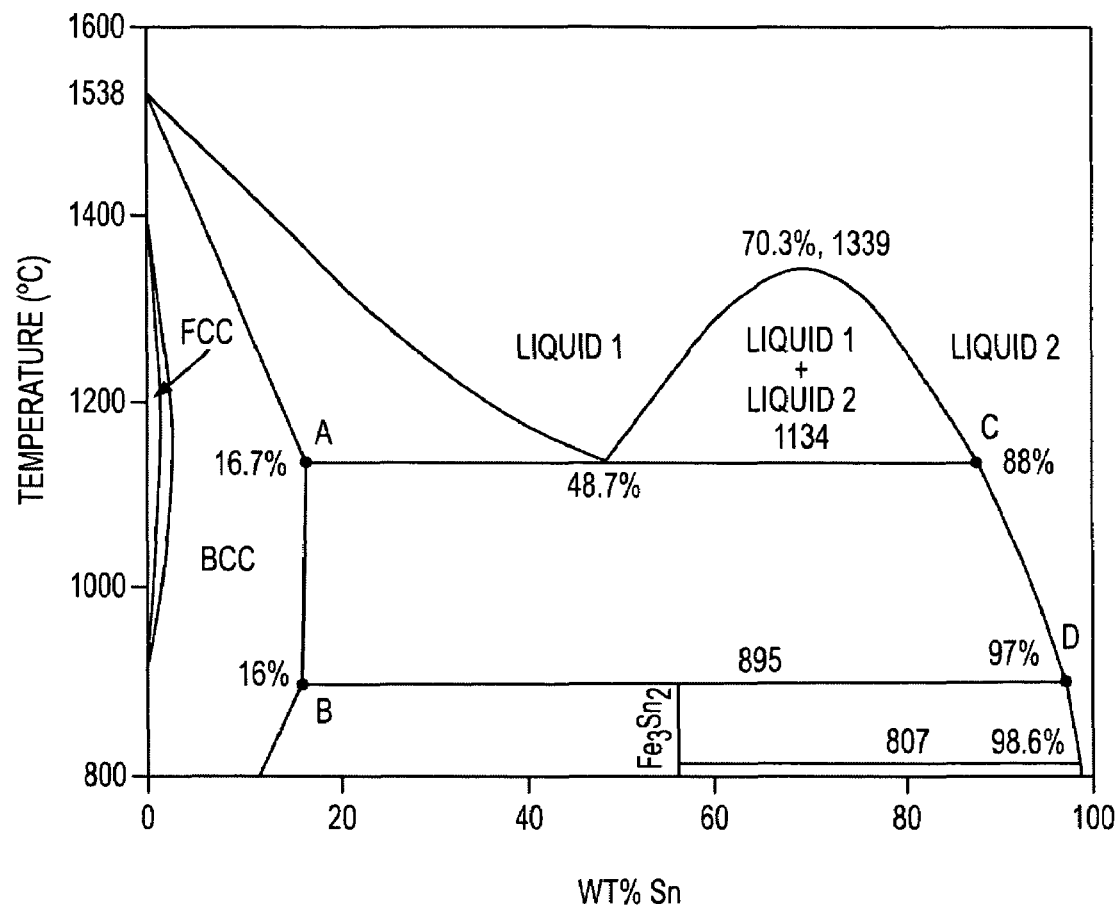
FIG. 2 illustrates a binary phase diagram for a tin-iron metal mixture that is useful in accordance with the present invention.

FIG. 2 illustrates a phase diagram for iron and tin adapted from Hari Kumar, K. C., et al., *Calphad*, 20, 2, 139-149 (1996). It can be seen from FIG. 2 that one effect of adding iron (the reactive metal) to tin (the diluent metal) is to substantially lower the melting temperature of the iron. The liquidus of the metal mixture decreases from 1538° C. (pure iron) to about 1134° C. at a melt composition of about 48.7 weight percent tin and 51.3 weight percent iron.

According to one embodiment of the present invention, it is preferred that the metal mixture be maintained at a temperature above the liquidus line AC of FIG. 2 (e.g., above 1134° C.). A metal-steam reaction temperature that is too high, however, adds significantly to the operating costs. For the completely molten iron/tin system illustrated in FIG. 2, the melt should be maintained at a temperature above the liquidus temperature of about 1134° C., more preferably at a temperature of at least about 1200° C. For the purpose of reasonable economics, the temperature should not be greater than about 1500° C. and more preferably is not greater than about 1400° C. A particularly preferred temperature range for the completely molten tin/iron metal mixture is from about 1200° C. to 1300° C. At 1200° C., about 50 weight percent iron dissolves in tin with sufficient superheat and the mixture stays in the molten state as iron is oxidized. Also, the reaction between steam and liquid iron dissolved in tin to form pure hydrogen at 1200° C. is also quite vigorous and the reaction kinetics are excellent. Furthermore, the thermodynamics for the steam/iron system at 1200° C. are relatively good, requiring an excess of only about 12.2 tons of steam to produce each ton of hydrogen (1.37 moles of steam per mole of hydrogen).

According to this embodiment, it is preferred that that the metal mixture initially include at least about 3 weight percent iron in the molten metal mixture, more preferably at least about 10 weight percent iron, even more preferably at least about 20 weight percent iron and most preferably at least about 50 weight percent iron in the molten metal mixture. Further, the amount of iron in the molten metal mixture should preferably not exceed about 85 weight percent and more preferably should not exceed about 80 weight percent. The balance of the metal mixture in a preferred embodiment consists essentially of tin. Accordingly, the amount of tin in the system is preferably not greater than about 97 weight percent, more preferably is not greater than about 90 weight percent and even more preferably is not greater than about 80 weight percent. The molten metal mixture preferably includes at least about 15 weight percent tin and more preferably at least about 20 weight percent tin.

According to another embodiment, insoluble phases such as in the form of particles can be dispersed within the molten metal. This assembly of a molten metal and an insoluble phase is termed a slurry. According to one embodiment, a portion of the steam is contacted with a slurry that includes a molten metal mixture and a solid second phase, wherein the solid second phase includes reactive metal-containing particles and is adapted to supply additional reactive metal to the molten metal mixture. Preferably, the particles are metallic particles (e.g., not oxide particles). For example, the slurry could include iron-rich metallic particles within an iron/tin melt that is saturated with iron. As the steam reduction process proceeds, dissolved iron is removed from the molten metal mixture by oxidation of the iron and additional iron from the iron-rich particles dissolves in the molten metal to keep the molten metal portion of the slurry saturated with iron.

Referring again to the phase diagram in FIG. 2, the composition within the two-phase region defined by point A (83.3 wt. % Fe at 1134° C.), point B (84 wt. %. Fe at 1134° C.), point C (12 wt. % Fe at 895° C.) and point D (3 wt. % Fe at 895° C.) includes an iron/tin melt with about 3 wt. % to 84 wt. % total iron, with a portion of the iron as iron-rich metallic particles dispersed in the melt. At a given temperature between about 895° C. and about 1134° C., as iron is removed from the molten metal due to iron oxidation, additional solid iron from iron-rich particles will dissolve, thereby maintaining the level of iron in the melt at bulk saturation until the solid iron is depleted. This replacement of iron that is lost to oxidation by iron originating from the iron-rich particles keeps the activity of the iron high, which, in turn, maximizes the production of hydrogen. For example, at a temperature of about 950° C. and about 50 wt. % total iron, the molten metal mixture will include about 4 wt. % dissolved iron in the system. As the dissolved iron is oxidized, additional iron metal from the iron-rich particles will dissolve to maintain 4 wt. % dissolved iron in the melt. The activity of the iron, therefore, remains unchanged as a consequence of dissolution of iron-rich particles.

Thus, according to this embodiment, the slurry, comprised of the molten metal mixture and iron-containing particles, is maintained at a temperature below the liquidus temperature of 1134° C. and is at least about 895° C., more preferably from about 900° C. to about 1134° C.

One advantage of such a method is that the activity of the iron remains constant and in fact is close to one, and therefore the production rate of hydrogen due to the reduction of steam remains constant and maximized throughout the process. The desired effect of constant activity of the reactive metal would also be observed if the process were carried out within the miscibility gap region of FIG. 2; however, the activity of iron would be somewhat less than one.

A thermodynamic relationship exists between the partial pressure of hydrogen in the off-gas, the reaction temperature and the weight percent iron in the molten metal composition. The thermodynamic quantity, referred to as the "activity" of iron, varies as a function of iron concentration and strongly influences the ratio of hydrogen to water in the off-gas. The production of hydrogen is maximized by operating within phase regions that establish a high iron activity over a wide composition range through the use of a second phase in equilibrium with the reacting phase. This applies both to the liquid-liquid region, above the line AC in FIG. 2, as well as the solid-liquid region, below the line AC and to the right of the line AB. However, the present invention does not exclude operation in the iron-rich liquid phase.

Figure 3:
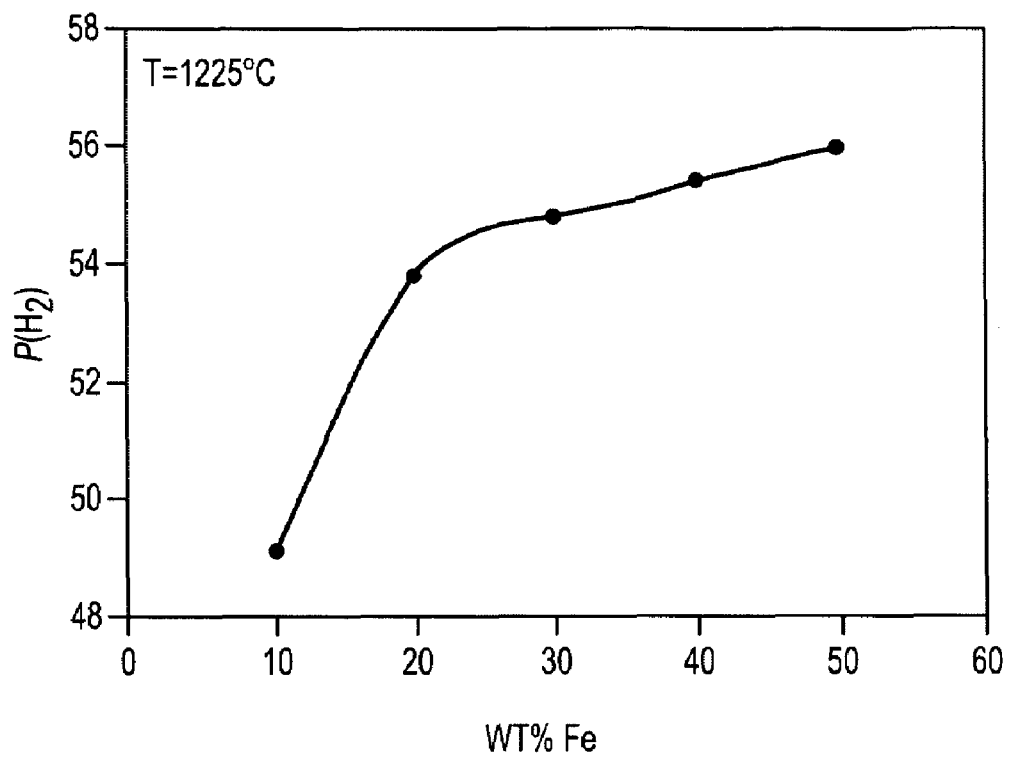
FIG. 3 illustrates the production rate of hydrogen as a function of iron content in the reactor according to an embodiment of the present invention.
Figure 4:
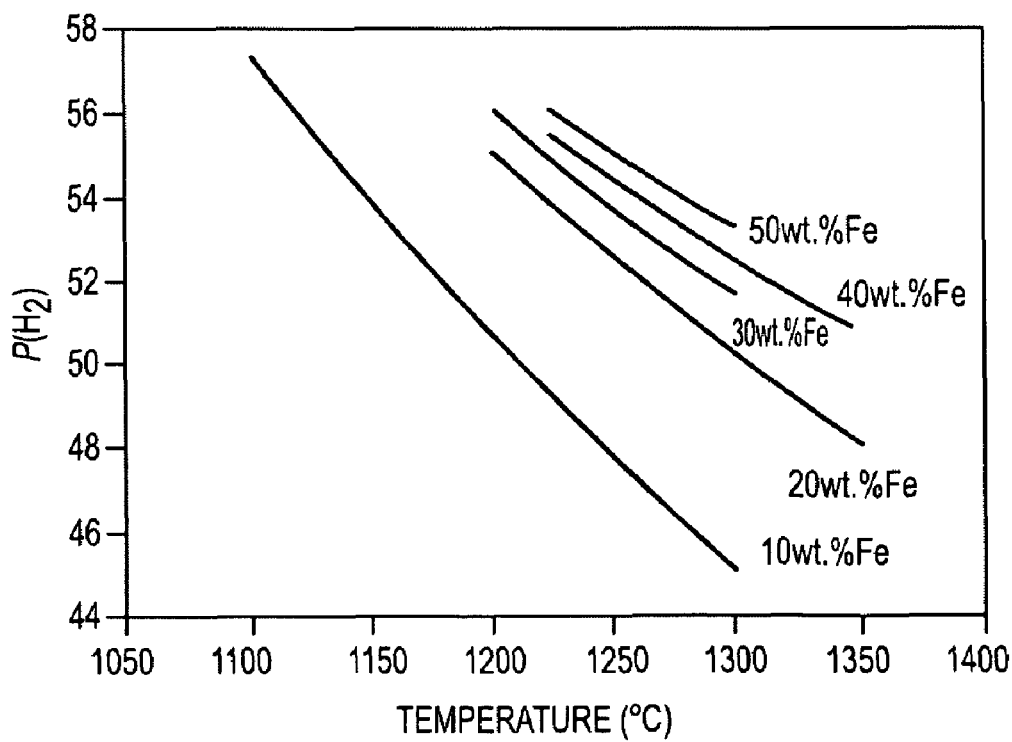
FIG. 4 illustrates the production rate of hydrogen as a function of iron content and reaction temperature according to an embodiment of the present invention.

FIG. 3 illustrates the relationship between the level of hydrogen in the off-gas as a function of iron content in the molten metal mixture and ignoring the reaction of the carbonaceous material. FIG. 3 was calculated based on thermodynamics of the steam/metal reaction at 1225° C. It is evident that the hydrogen production rate rapidly decreases as the iron content drops from 20 weight percent to 10 weight percent. FIG. 4 illustrates the hydrogen production as a function of temperature and iron content, again ignoring hydrogen production due to reaction of the carbonaceous material.

At levels below about 20 weight percent iron and temperatures above about 1134° C., the production capacity for hydrogen is impaired since: (1) the $pH_2/pH_2O$ drops significantly; and (2) only short periods of time are available before gas flows (i.e., steam and metal oxide reductant) have to be switched.

The reactor temperature can be controlled to maintain a substantially constant temperature by controlling the incoming steam temperature and quantity and/or by adding oxygen to the reactor, as is discussed in more detail below.

The reactor can be maintained at an elevated pressure if necessary for adequate steam residence time in the reactor. For example, it may be desirable to maintain an elevated pressure, such as about 2 atmospheres (about 29 psi). Syngas typically requires several stages of compression to secure the high pressures required for either transmission by pipeline or as a first step in the subsequent synthesis of hydrocarbons (a methane synthesis loop for example). Operating the reactor at slightly elevated pressure (2 atmospheres, for example) significantly reduces the capital and energy cost associated with the first stage of compression. The high cost of the first stage of compression is related to the low density of the hydrogen-rich syngas. However, significantly increased pressure in the reactor adds to capital cost and therefore the pressure in the hydrogasification reactor is preferably not greater than about 3 atmospheres (about 44 psi).

According to the present invention, a slag layer is maintained over the molten metal mixture. A slag layer provides a number of advantages, including preventing the metal oxide, e.g., iron oxide, from exiting the reactor. The temperature in the hydrogasification reactor should be sufficient to maintain the slag layer that forms over the metal mixture in the molten state over a range of compositions. For a mixed metal system, as the reactive metal is oxidized a decrease will occur in the concentration of the reactive metal in the metal mixture and the metal mixture should remain molten as the reactive metal is oxidized. Similar to the range of compositions for the molten metal discussed previously with respect to FIG. 2, the range of slag compositions required to ensure adequate slag fluidity and reactivity, and prevent foaming can be adjusted, as necessary, for a given temperature. For example, fluxes can be added to the reactor to adjust the properties of the slag. One flux system is indicated by the liquid surface of $SiO_2$, $FeO$, $CaO$, $MgO$, $Na_2O$ and $K_2O$. However, sulfur and other cations may be incorporated in this or other slags to secure satisfactory slag chemistry.

The metal oxide (e.g., wüstite and/or magnetite) that is generated by steam reduction can advantageously be trapped (dissolved or suspended) in a slag layer within the reactor. At the preferred temperatures, the metal oxide is incorporated into the slag, which is lighter than the metal mixture. Therefore, as the dissolved metal is depleted from the molten metal mixture, the metal oxide rises through the molten metal and contributes to the slag layer on top of the molten metal. It is an advantage of this embodiment of the present invention that the oxide formed upon reaction of the reactive metal with the steam has a density that is less than the density of the molten metal, whereby the metal oxide rises to the slag layer. Preferably, the metal oxide is at least about 10 percent less dense than the molten metal. This also enables the metal to sink from the slag layer to the molten metal mixture upon reduction of the metal oxide. This accumulation of iron oxide in the slag may require the addition of a flux such as $SiO_2$, $FeO$, $CaO$, $MgO$, $Na_2O$, $K_2O$ or mixtures thereof to maintain the slag in the preferred condition with respect to viscosity, reactivity, foaming, and the like.

Accordingly, a portion of the steam introduced to the hydrogasification reactor is reduced by reaction with the reactive metal to form a metal oxide. In addition to the steam, a carbonaceous material is also injected into the molten metal and a second portion of the steam reacts with the carbonaceous material to form carbon monoxide and hydrogen. The carbonaceous material can include crude oil, tar sand or a similar substance, pet coke, municipal waste, hazardous waste, biomass, tires and/or any combination thereof. In a preferred embodiment, the carbonaceous material includes coal and the following description refers to coal as the carbonaceous material, although it will be understood that the present invention is not limited thereto. The coal can be a low-grade coal as well as a high-grade coal. The coal can optionally be pre-treated such as by comminuting the coal to reduce the particle size of the coal, although the particle size of the coal or other carbonaceous material is not critical to the practice of the present invention.

The reactants (e.g., steam, coal and molten metal) must be contained within a suitable reactor and maintained under suitable reaction conditions. Further, the reactants should be provided in a manner conducive to good mixing and high contact surface area. High-temperature reactors suitable for establishing good gas/liquid contact are utilized in the chemical, and especially metallurgical industries.

For example, bath smelting reactors can be used for carrying out the method of the present invention. Bath smelters have been used for the efficient reduction of iron oxides (e.g., fine iron ore and iron-rich secondary materials)

using carbonaceous materials, including those other than metallurgical coke, for reduction. The reactants are typically injected into a molten metal bath using a water-cooled lance. Examples include the Hismelt technology, such as described in U.S. Pat. No. 3,751,019 by Phillips and the Ausmelt technology, such as described in U.S. Pat. No. 5,282,881 by Baldock et al. Each of these U.S. patents is incorporated herein by reference in its entirety. These systems advantageously utilize a stationary lance, enabling the reactor to be sealed for operations at elevated pressures, if necessary.

One reactor system that is useful according to the present invention utilizes a top-submerged lance (TSL) to inject the steam into the molten metal below the surface of the molten metal. Such reactors have been used for the commercial production of tin from tin ore (cassiterite). Examples of reactors utilizing a top-submerged lance to inject reactants are disclosed in U.S. Pat. No. 3,905,807 by Floyd, U.S. Pat. No. 4,251,271 by Floyd, U.S. Pat. No. 5,251,879 by Floyd, U.S. Pat. No. 5,308,043 by Floyd et al. and U.S. Pat. No. 6,066,771 by Floyd et al. Each of these U.S. patents is incorporated herein by reference in their entirety. Such reactors are capable of injecting reactants (e.g., steam) into the molten metal at extremely high velocities, approaching Mach 1, thereby promoting good mixing of the reactants. Although the following description refers to the use of a reactor including a top-submerged lance, it will be appreciated that other types of reactors can be utilized in accordance with the present invention.

Figure 5:
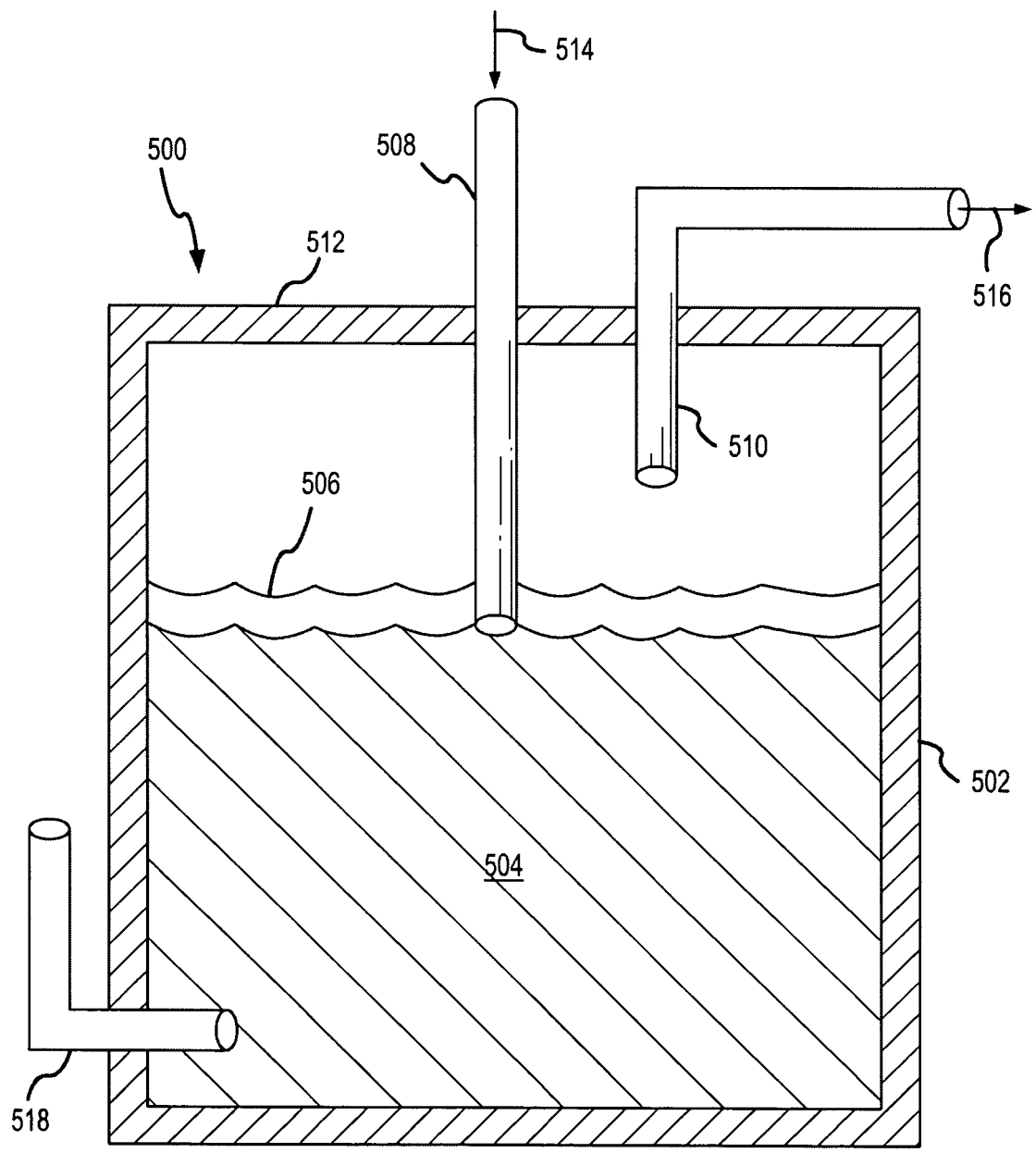
FIG. 5 illustrates a reactor that is useful according to an embodiment of the present invention.

The major function of the top submerged lance (TSL) furnace is to maximize contact between the solids, liquids and gases. FIG. 5 is a schematic illustration of such a reactor. The reactor 500 includes refractory sidewalls 502 that are adapted to contain the molten metal 504. A side-penetrating lance 518 penetrates the furnace near the bottom of the reactor and is provided for the optional introduction of oxygen for the purpose of heating the reactor 500. A top-submerged lance 508 is disposed through the reactor top wall 512 and is adapted to inject coal entrained by steam into the metal 504 at a high velocity. Preferably, the top-submerged lance 508 terminates and injects steam and coal below the surface of the slag layer 506 and near the interface of the molten metal 504 and the slag layer 506.

The temperature of the steam-entrained, particulate coal increases rapidly from ambient temperature to the reactor temperature. Caking of the coal particles is not a significant issue since the particles have virtually no opportunity to coalesce before passing the temperature region where caking can occur. Rapid devolatilization of the coal particles occurs as the particles approach the reactor temperature.

When the coal and steam come in contact with the molten metal 504, a series of physical and chemical reactions occur. According to the present invention, a portion of the steam reacts with the reactive metal producing hydrogen and a metal oxide, and the metal oxide rises and is incorporated into the slag, as is discussed above.

At temperatures above 800° C., the coal partitions into volatile matter and coke or char comprised of the fixed carbon and ash. The volatile matter reacts with the steam to form hydrogen and carbon monoxide. These products are the sum of the reactions given in Equations 1, 5 and 7, although Equation 7 proceeds in the opposite direction shown and is known as the steam methane reformation reaction. The volatiles disproportionate into methane and carbon and both of these species react with steam to produce hydrogen and carbon monoxide, respectively.

The steam also reacts with carbon contained in the coke (or char) to form hydrogen and carbon monoxide. This highly endothermic reaction (Equation 5) requires heat, which can be provided in at least four ways, which are described in detail below.

The formation of hydrogen by reduction of a portion of the steam with the reactive metal enables control of the $H_2$:CO ratio in the synthesis gas that is extracted from the reactor. That is, a variable amount of hydrogen is produced by the steam/reactive metal reaction, variable in proportion to the quantity of steam used and a mixture of hydrogen and carbon monoxide are formed in a fixed proportion by the steam/hydrocarbon reaction, which is dependant upon the reactor temperature, the quantity of coal and steam (and oxygen, if any) employed and the type of coal. Thus, sufficient steam is provided to react with both the coal and with the reactive metal. The foregoing reactions proceed until the reactive metal is oxidized to a lower limit, established by economics. At this point the introduction of steam is stopped and, after purging, a reductant (e.g., coal and air) is introduced into the reactor for the purpose of reducing the metal oxide back to the metal.

The regeneration of the reactive metal from the metal oxide can occur in a number of ways. In one preferred embodiment, carbon from the devolatilization of coal is used as a reductant (volatile matter from this devolatilization may be directed to the gasification reactor.). The carbon entering the metal oxide regeneration reactor is contacted with the metal oxide dissolved in the slag layer and reacts to form the reactive metal and carbon monoxide. The metal gravitates to the molten metal bath where it replaces the reactive metal first reacted with steam. The carbon monoxide rises through the molten metal and fluid slag into the freeboard (open space) above the charge. Air is introduced into this space and the carbon monoxide is oxidized by the air to carbon dioxide, releasing significant quantities of heat. Also, if the volatiles released by the devolatilization of the coal are not directed to the gasification reactor, they can be combusted, releasing additional heat. This heat is required to maintain the carbon/metal-oxide reaction and compensate for furnace heat losses.

For the coal hydrogasification reactions to proceed continuously, a heat balance must be achieved around the gasification reactor. That is, heat brought into the reactor by the feed materials plus heat generated by chemical reactions within the reactor must equal heat leaving with the products plus heat leaving as environmental losses. For coal hydrogasification, heat must be supplied. Admitting oxygen into the reactor is one method for producing heat, and the amount of heat produced is proportional to the amount of oxygen introduced, which permits control over the reactor temperature.

At least two techniques for introducing oxygen into the furnace are possible according to the present invention. The oxygen can be introduced down the top-submerged lance 508 with the steam and coal, or can be introduced independently at some other location, such as by side-penetrating lance 518.

However, the use of oxygen to generate heat in the reactor consumes a substantial quantity of the reactive metal, leaving less iron available for generating hydrogen. The reduction in hydrogen availability means that less coal can be admitted to the reactor if the specified $H_2$:CO is to be maintained. Accordingly, less synthesis gas is produced and the cost of utilizing oxygen for heat is about twice the cost of superheating the melt.

The melt (slag and molten-metal mixture) can be superheated during the regeneration of the reactive metal. Thus, reactor 500 can contain a superheated melt at the start of its cycle. As the chemical reactions proceed in reactor 500, and because insufficient heat is available to maintain the temperature, the temperature begins to fall. As the temperature decreases, some of the sensible heat of the melt is released supplying the heat needed in reactor 500. The amount of sensible heat released is a product of the specific heats of the molten metal and slag multiplied by their masses and multiplied by the temperature decrease.

Controlling either or both the mass of melt that is superheated and the temperature of the superheat can control the amount of sensible heat gained and then released. To preserve the life of the refractory bricks lining of reactor 500, it is desirable to minimize the temperature swing. The mass of melt, correspondingly, must be increased to maintain the same sensible heat gain/loss. For example, assume that reactor 500 is six meters in diameter and a superheat of 237° C. is needed to impart the sensible heat required for heat balance. A preferred method to supply the same amount of sensible heat but with far less thermal shock to the refractory bricks is to increase the diameter of reactor 500 to eight meters (i.e., oversize the reactor in relation to the other process equipment) and provide a superheat of only 100° C. This is possible because the mass of melt in an eight-meter diameter reactor is 2.37 times the mass of melt in a six-meter diameter reactor, assuming geometric similitude between reactors.

The larger mass of metal and slag in the oversized (e.g., eight-meter diameter) reactor affords several advantages in addition to assisting in the heat balance about the reactor. The larger mass of melt and slag means that the variation of the percent reactive metal oxide in the slag and reactive metal in the melt can vary between narrower limits than for the smaller mass of slag and melt. These narrower limits are advantageous because the thermodynamic activity of the reactive metal and reactive metal oxide remain closer to unity, which facilitates the reactions. Alternatively, the larger mass of melt and slag can permit longer cycle times. Also, the larger mass of melt will permit increased production of hydrogen, syngas or ammonia, thereby shortening cycle times and effectively lowering capital cost.

The hydrogasification process is continued until the quality of the synthesis gas decreases to a sufficiently low level. Typically, this will result from a depletion of the reactive metal and a resulting decrease in the hydrogen content of the synthesis gas. At this point, the injection of steam is terminated and a reductant is introduced into the reactor containing the molten metal and the slag to reduce the metal oxide back to the metal In this regeneration step, which can be viewed as reductive cleaning of the slag, the metal oxide in the slag is reduced and returned to the melt as the reactive metal. This is achieved by lowering the oxidation potential of the system through introduction of reductant to the reactor. The reductant can be carbon monoxide, which is preferable when operating at temperatures below 1000° C., or carbon derived from coal, petroleum coke, waste, other carbon source, which is preferable above 1000° C. According to a preferred embodiment, operating at a temperature above 1000° C., the oxidation potential of the system is lowered by injecting particulate carbon, hydrocarbon or liquid hydrocarbon into the melt under conditions of intense mixing. The particulate carbon or hydrocarbon is preferably coke, but may include coal or other organic material. A liquid hydrocarbon, such as #6 or other oil can also be used. Waste materials such as scrap tires, biomass, animal waste, or municipal waste may also be used.

Prior to injection of a reductant, the reactor may be purged, such as with steam, to remove any gases from the reactor. After the reductive cleaning of the slag is complete, the reactor may again be purged, with air or steam, for the purpose of removing any carbon that may be dissolved in the metal and/or for the purpose of removing any other tramp elements that may be in either the melt or slag and that otherwise would contaminate the synthesis gas.

Figure 6:
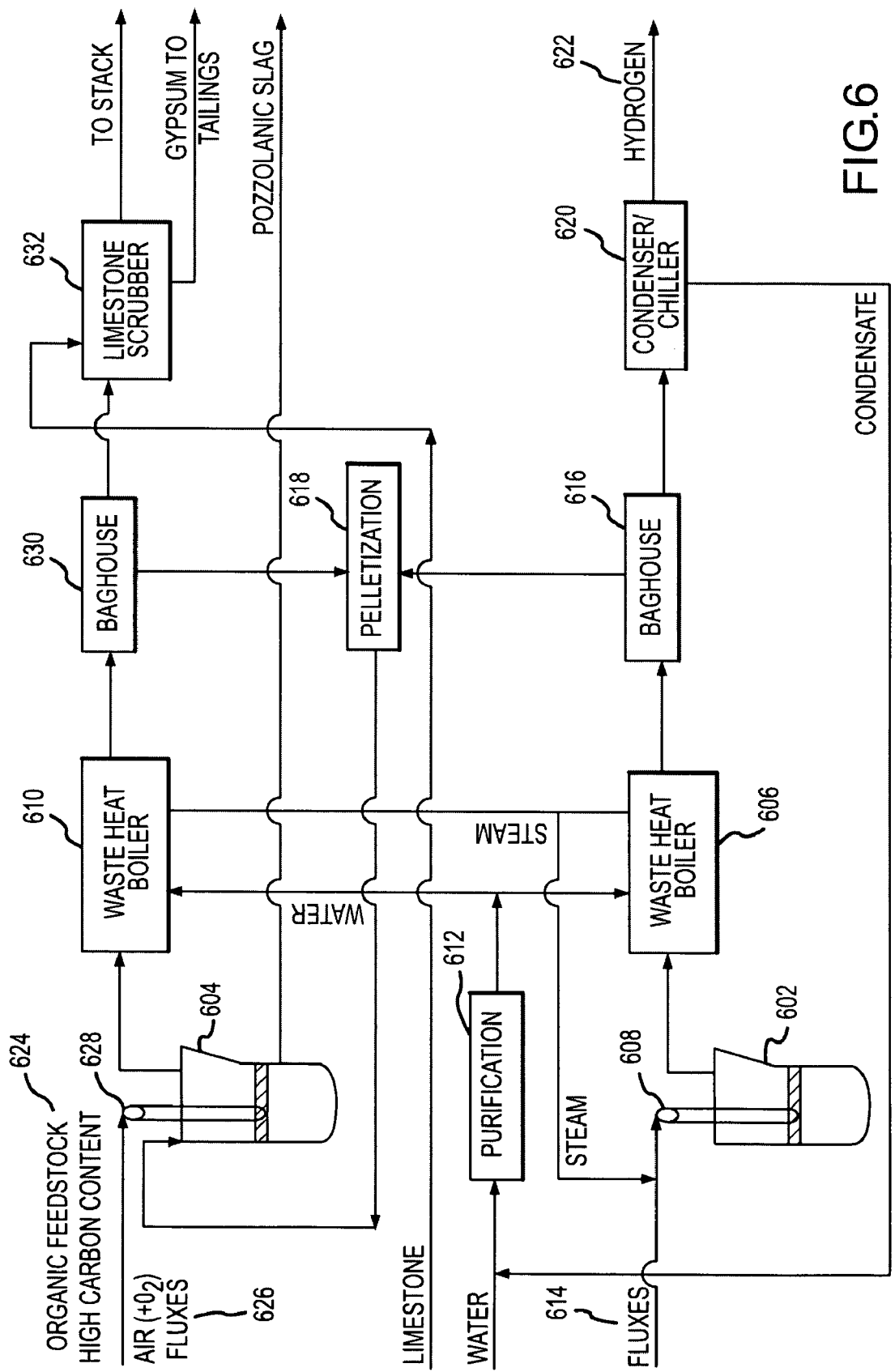
FIG. 6 illustrates a process flow for continuous hydrogen production.

FIG. 6 illustrates a process for continuous generation of hydrogen using two reactors as disclosed in the co-pending U.S. patent application Ser. No. 10/085,436 entitled "Method for the Production of Hydrogen and Applications Thereof," and incorporated herein by reference in its entirety.

The hydrogen generation process employs two reactors 602 and 604 wherein one of the reactors operates in steam reduction mode while the other operates in metal oxide reduction mode. As illustrated in FIG. 6, the reactor 602 is operating in steam reduction mode and generates hydrogen, and reactor 604 is operating in metal oxide reduction mode, wherein the reactive metal is iron.

Steam is provided by heating water in waste heat boilers 606 and 610. Prior to heating in the boilers, the water should be subjected to purification 612 such as by using reverse osmosis and de-ionization to remove contaminants that can affect boiler operation or introduce impurities into the hydrogen product gas. Steam is produced in the boilers and is provided to the reactor 602 at a super-heated temperature that is sufficient to maintain isothermal conditions within the steam reduction reactor 602 at the operating temperature, e.g., about 1200° C.

The steam is injected into the reactor 602 through a top-submerged lance 608. The top-submerged lance provides good mixing and a high contact surface area between the steam and the molten metal mixture to promote the steam reduction/metal oxidation reaction. The reactor 602 is sealed to prevent egress of hydrogen and steam from the reactor. Also, the reactor may be placed under modest pressure to provide a sufficient contact time for the steam and to deliver the hydrogen under pressure.

Other materials can be added to the reactor if necessary. For example, fluxes 614 can be added to control the properties of the slag layer that forms above the molten metal mixture as the steam reduction reaction oxidizes the metal. Possible fluxes include $SiO_2$, FeO, CaO, MgO, $Na_2O$ or $K_2O$. Additionally, other materials such as tin compounds, cassiterite ore or other materials such as iron compounds or ore may be added to make-up for losses of metal values. According to a particularly preferred embodiment, cassiterite ore ($SnO_2$) is injected into the reactor to make-up for tin losses.

A hydrogen-containing gas that includes hydrogen and excess steam is removed from the reactor 602. The hydrogen-containing gas can be passed through the waste heat boiler 606 to provide heat for additional steam, thereby conserving heat values. The hydrogen-containing gas stream can also include some contaminants, such as the sub-oxide of tin oxide (SnO), the hydrated sub-oxide of tin ($SnO_2H_2$), and entrained particulates of (frozen) slag which are ejected from the molten metal bath and slag, and such contaminants can be removed in a baghouse 616. For example, the volatile tin compounds can be condensed from the gas stream and along with particulate slag can be captured either in the waste heat boiler or in the baghouse. After being captured, these materials can be pelletized 618 and optionally provided to either reactor 602 operating in steam reduction mode or reactor 604 operating in the metal oxide reduction mode for recovery of metal values and control of the slag chemistry. After removal of contaminants, if any, the hydrogen gas stream is treated in a condenser 620 and/or chiller to condense the excess steam from the hydrogen gas stream and form a high purity hydrogen gas stream 622. Water condensed from the hydrogen gas stream can be recycled for additional steam production.

Simultaneously, metal oxides are reduced in reactor 604. The metal oxides are reduced by a reductant as is described above, such as carbon or carbon monoxide according to the following chemical equations:

(13)

(14)

Carbon may be derived from virtually any carbonaceous material such as coal, petroleum coke, biomass and organic waste materials, including municipal waste and hazardous waste. It is possible to add the carbonaceous material into the reactor 604 by simply dropping it in the reactor. Carbon monoxide can be formed by injecting coal 624 or other carbonaceous material and oxygen 626 through a top-submerged lance 628. As with reactor 602, the top-submerged lance 628 provides good mixing and contact surface area between the reactants. The oxygen-containing gas is also preferably injected using a top-submerged lance or similar device.

Air is admitted above the metal/slag charge for the purpose of combusting any carbon monoxide that may be present. This combustion reflects heat back down into the melt where it is needed for the metal oxide reduction reaction. Further, the presence of a small excess of air (typically 3 percent) precludes discharge of carbon monoxide into the atmosphere.

The ash-forming minerals that are typically part of the coal (or other carbonaceous material) used as a reductant contribute to the slag layer within the reactor 604. When coal (or other carbonaceous material) is used as feedstock 624 and there is adequate calcium oxide (CaO) in the slag, the slag layer can be a salable pozzolanic by-product. As with reactor 602, other materials such as fluxes can be injected into the reactor 604, for example to control the properties of the slag such as slag fluidity or tendency to foam. The off-gas from the metal oxide reduction reactor 604 can include carbon dioxide, nitrogen and some contaminants from the coal such as sulfur. Heat from the off-gas can be conserved in the waste heat boiler 610 where steam is generated. The gas stream can then be treated in a bag-house 630 to remove particulate contaminants. The remaining gases can be treated in a limestone scrubber 632 to form environmentally benign stack gases and gypsum from the sulfur that originates from the coal. Alternatively, the sulfur can be scrubbed with aqueous ammonia to form ammonium sulfate, a useful compound for fertilizing soil.

Thus, as iron is depleted from the molten metal mixture in the steam reduction reactor 602, and as the iron oxide is reduced to metal in the metal oxide reduction reactor 604, their functions can be reversed by switching the flows into the reactors and the flows of the cooled gases after the waste heat boilers. Prior to switching gas flows, the reactors can be purged to remove residual gases and contaminates, if any. Accordingly, hydrogen gas can be produced in a substantially continuous manner.

Figure 7:
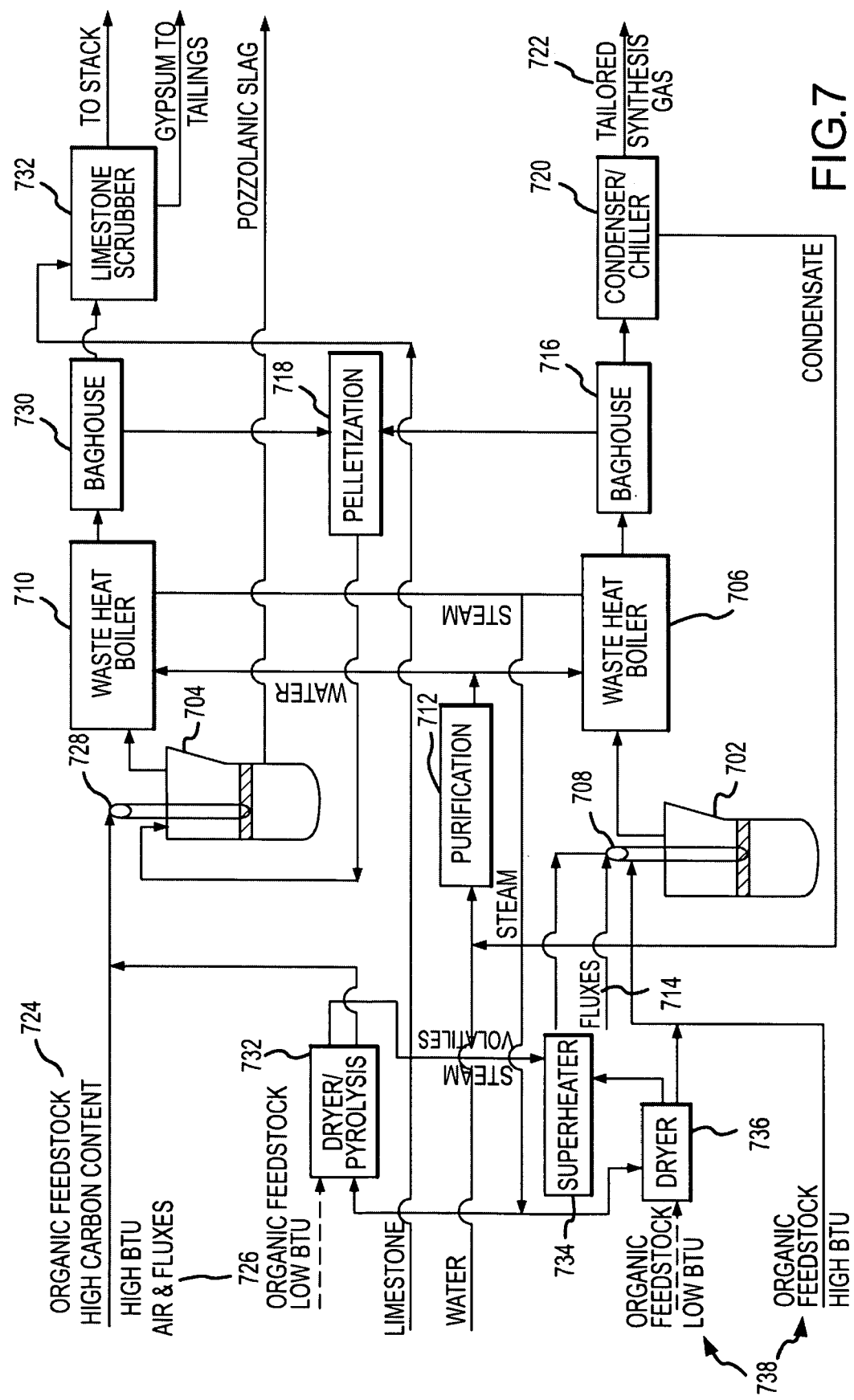
FIG. 7 illustrates a process flow for continuous synthesis gas production according to an embodiment of the present invention.

FIG. 7 illustrates a process flow for continuous synthesis gas production according to an embodiment of the present invention to produce a tailored $H_2$:CO ratio syngas. Hydrogen, added by the steam-iron reaction, supplements the hydrogen produced by gasification to increase the overall $H_2$:CO ratio.

A tailored synthesis gas can be produced if both a carbonaceous material and steam are fed into the reactor that normally receives only steam for the purpose of making hydrogen, i.e., reactor 602 in FIG. 6. For hydrogen production, only the reactor operating in metal oxide reduction mode receives carbonaceous material, while for gasification according to the present invention, both reactors receive carbonaceous material.

Referring again to FIG. 7, the synthesis gas generation process employs two reactors 702 and 704 wherein one of the reactors operates in steam reduction and gasification mode while the other operates in metal oxide reduction mode. As illustrated in FIG. 7, reactor 702 is operating in steam reduction mode and generates tailored synthesis gas 722 and reactor 704 is operating in metal oxide reduction mode.

Steam is provided by heating water in waste heat boilers 706 and 710. Prior to heating in the boilers, the water should be subjected to purification 712 such as by using reverse osmosis and de-ionization to remove contaminants that can affect boiler operation or introduce impurities into the synthesis product gas. Steam is produced in the boilers and is provided to the reactor 702 at a super-heated temperature that is sufficient to support a heat balance about reactor 702.

A carbonaceous material 738 is provided to the reactor 702. If the carbonaceous material is a high Btu carbonaceous material, such as comminuted scrap tires or high-rank coal, it is fed into the reactor 702 through the submerged lance 708. However, if the carbonaceous material is a low to medium Btu feedstock, such as municipal waste, animal waste, sewage sludge, low-rank coals, biomass or other medium to low Btu organic materials it must first be dried in a dryer 736.

Steam is injected into the reactor 702 through a top-submerged lance 708. The top-submerged lance 708 provides good mixing and a high contact surface area between the steam, carbonaceous material and the molten metal to promote the steam reduction/metal oxidation reaction and the steam-carbon reaction. The reactor 702 is sealed to prevent egress of hydrogen, carbon monoxide and steam from the reactor (see FIG. 5). Also, the reactor may be placed under modest pressure to provide a sufficient contact time for the steam and to deliver the synthesis gas under pressure.

Other materials can be added to the reactor 702 if necessary or desired. For example, fluxes 714 can be added to control the properties of the slag layer that forms above the molten metal mixture as the steam reduction reaction oxidizes the metal. Possible fluxes include $SiO_2$, FeO, CaO, MgO, $Na_2O$ or $K_2O$. Additionally, other metal-containing materials such as tin compounds, cassiterite ore or other materials such as iron compounds or ore may be added to make-up for losses of metal values. According to a particularly preferred embodiment, cassiterite ore ($SnO_2$) is injected into the reactor to make-up for tin losses when tin is used as a reactive metal or a diluent metal. A synthesis gas that principally includes hydrogen, carbon monoxide, carbon dioxide and excess steam is removed from the reactor 702. The synthesis gas can be passed through a waste heat boiler 706 to provide heat for additional steam, thereby conserving heat values.

The synthesis gas stream can also include some contaminants, such as the sub-oxide of tin (SnO), the hydrated sub-oxide of tin ($SnO_2H_2$), entrained particulates of (frozen)

slag and gaseous compounds that may be formed from trace constituents associated with the carbonaceous material. Such contaminants can be removed in a baghouse 716. For example, the volatile tin compounds can be condensed from the gas stream and, along with particulate slag, can be captured either in the waste heat boiler 706 or in the baghouse 716. After being captured, these materials can be pelletized 718 and optionally provided to the reactor 702 operating in steam reduction mode or, preferably, the reactor 704 operating in metal oxide reduction mode for recovery of metal values and control of the slag chemistry. Noxious gases derived from trace constituents in the carbonaceous feedstock can be removed by scrubbing.

After removal of contaminants, if any, the synthesis gas stream is treated in a condenser 720 and/or chiller to condense the excess steam from the synthesis gas stream and form a high purity tailored syngas stream 722. Water condensed from the synthesis gas stream can be recycled for additional steam production. The tailored syngas can then be converted to methane or methanol in a catalytic conversion unit (not illustrated).

Simultaneously, metal oxides are reduced in the reactor 704. The metal oxides preferably are reduced by a reductant such as carbon, which can be formed by injecting a carbon-containing feedstock 724 directly into the reactor 704, such as through a top-submerged lance 728. As with reactor 702, the top-submerged lance 728 provides good mixing and contact surface area between the reactants.

Carbon and heat are required to regenerate the iron in the reactor 704. Feedstocks containing a large percentage of carbon are preferable. Petroleum coke, particularly petroleum coke including over 80 percent carbon is preferred. Char, the residue from coal or low-Btu organic feedstocks, can also be used. The organic feedstock (coal or other carbonaceous material) may be pyrolyzed in dryer/pyrolyzer 736, with the volatiles from the pyrolysis directed to the reactor 702 to provide heat to reactor 702, resulting from their (volatiles) reaction with steam, and to offset some portion of the heat-consuming steam-carbon reaction. Dryer/pyrolyzer 736 may be for example a fluid bed combustor that uses oxygen and steam at about 1000° C. to supply the heat required to dry the coal and boil-off (expel) the volatiles.

That portion of the carbon in the carbonaceous material used to reduce the metal oxide is transformed into carbon monoxide. This carbon monoxide is burned with air above the molten metal, reflecting heat back to the interior furnace walls and the molten metal. A portion of the carbon feedstock can be burned to provide the requisite thermal energy.

Ash-forming minerals are typically part of the organic feedstock (or other carbonaceous material) that is employed along with oxygen to bring about the reduction of the reactive metal oxides. Such ash-forming minerals contribute to the slag layer within the reactor 704.

As is discussed above with respect to reactor 702, other materials can be injected into the reactor 704. For example, fluxes can be injected to control the properties of the slag such as slag fluidity or tendency to foam. The off-gas from the metal oxide reduction reactor 704 can include carbon dioxide, nitrogen and some contaminants from the coke, such as sulfur. Heat from the off-gas can be conserved in the waste heat boiler 710 where steam is generated. The gas stream can then be treated in a bag-house 730 to remove particulate contaminants. The remaining gases can be treated in a limestone scrubber 732 to form environmentally benign stack gases and gypsum ($CaSO_4.2H_2O$) from the sulfur that originates from the coal. Alternatively, the sulfur can be scrubbed with aqueous ammonia to form ammonium sulfate (($NH_4)_2SO_4$), a useful compound for fertilizing soil.

To conserve heat it may be desirable to keep the synthesis gas stream exiting the baghouse at its elevated temperature (400° C. to 500° C.) prior to being converted into methanol or methane. To do so, anhydrous ammonia may be injected into the gas stream to react with the acid gas components producing ammonium sulfide (($NH_4)_2S$), ammonium chloride ($NH_4Cl$) and ammonium fluoride ($NH_4F$). The ammonium salts that are produced may be removed from the gas stream, for example by pulsed ceramic filters. Thereafter, the purified gas stream can proceed directly to a conversion step without significant reheating.

Thus, as iron is depleted from the molten metal mixture in the steam reduction reactor 702, and as the iron oxide is reduced to metal in the metal oxide reduction reactor 704, their functions can be reversed by switching the flows into the reactors and switching the gas flows downstream of the waste heat boilers. Prior to switching gas flows, the reactors can be purged to remove residual gases and contaminates, if any. Accordingly, a syngas with a pre-chosen $H_2$:CO can be produced in a substantially continuous manner.

A combination of factors is required to achieve a heat balance across both of the reactors 702 and 704. First, reactor 704 incurs an increase in temperature of about 125° C. over the period of time that is required to reduce the iron oxide. Providing this increase only requires slightly increasing the fuel and air sent to reactor 704. This means that at the start of its cycle, reactor 702 is superheated by about 125° C. Over the period of time that is required for the iron in reactor 702 to be oxidized by steam, the sensible heat of the charge in 702 is given up thereby supplying heat to support the hydrogasification chemistry. Second, the steam is preferably superheated to at least about 1000° C. to bring additional heat into reactor 702. Third, volatiles derived from the carbonaceous feedstock destined for reactor 704 are diverted into reactor 702. This supplants some portion of the endothermic steam/carbon reaction for producing hydrogen and carbon monoxide with the exothermic steam-volatiles reaction thereby lessening the heat requirement for reactor 702 and adding heat to that reactor. For heat balance reasons, organic feedstocks such as municipal waste, animal waste, sewage sludge, low-rank coals, biomass and other medium to low Btu organic materials must first be dried by dryer/pyrolyzer 736. Steam is available from waste process heat and can be used as a drying medium. Steam will also carry odors, frequently a problem in drying materials such as animal waste, into the reactor 702 where organics are converted to simple non-malodorous molecules ($H_2$, CO & $CO_2$) as part of the gasification process. Various methods available for providing a heat balance are described below.

In a preferred embodiment according to the present invention, a reductant derived from the dryer/pyrolyzer 732 is injected into the molten metal and slag layer in the reactor 704. The feedstock can be injected through the top-submerged lance with the air, or can be added separately. It is particularly advantageous to use coke pyrolyzed from coal as the reductant source, because it is both abundant and relatively inexpensive compared to oil and gas. The use of scrap tires and other waste materials as feed for the reactor 704 can also supply some iron (e.g., from the steel belts). The metal oxide reduction process is continued until a sufficient amount of metal has been re-dissolved in the molten metal.

Preferably, the reaction conditions when operating in the mode to reduce the metal oxide to metal are substantially identical to the conditions during hydrogasification. That is, it is preferred that the temperature and pressure of the reactor 704 are the same or very similar to the temperature and pressure of the reactor 702. Thus, the temperature is preferably at least above the liquidus of the molten metal mixture (e.g., about 1134° C. for the tin/iron system) and in one embodiment is at least about 1200° C. Preferably, the temperature does not exceed about 1600° C. and more preferably does not exceed about 1400° C. In a particularly preferred embodiment, the temperature is about 1400° C. in reactor 702 and 1300° C. in reactor 704 at the start of their cycles, decreasing to 1300° C. in reactor 702 and increasing to 1400° C. in reactor 704 by the end of their cycles. The pressure should be slightly above atmospheric pressure in the reactor 702 and may be either slightly above or slightly below atmospheric pressure in the reactor 704. A preferred option is to operate both reactors at from about 1 to 2 atmospheres.

The steam-iron reaction in the reactor 702 produces hydrogen and a modest amount of heat. This heat of reaction is insufficient to offset furnace heat loss and provide a heat balance in the reactor 702. Therefore, as noted above, volatiles from the pyrolysis of organic feedstock of reactor 704, are directed to reactor 702 to help maintain the heat balance. Further, steam is admitted to reactor 702 at as high a temperature as is practicable, such as up to about 1000° C.

In the reactor 702 there are three reactions that produce hydrogen. The first two are operative all the time and include the modest heat-producing steam-iron reaction (Equation 12) described above, and the highly endothermic steam-carbon reaction (Equation 5). The third is the exothermic steam-volatiles reaction.

The benefit of the third reaction relative to heat balance depends upon the amount of volatiles being admitted into reactor 702. To maximize the amount of volatiles, feedstock to the reactor 704 is pyrolyzed and the released volatiles are directed into the reactor 702. Pyrolysis of the feedstock disproportionates the feedstock into: (1) char, principally composed of carbon and ash, directed to the reactor 704 for reducing the metal oxide; and (2) volatile matter (volatiles) comprised predominantly of carbon, hydrogen and oxygen, directed into the reactor 702. When the volatile matter reaches the temperature in the reactor 702 and steam is present, it is immediately rendered into hydrogen and carbon monoxide with the release of heat.

The steam-carbon reaction (Equation 5) is the principal gasification reaction. To sustain this endothermic reaction, a significant amount of heat must be furnished to the reactor 702. The required heat can be supplied to the reactor in at least four ways:

1. Oxygen can be added to the reactor 702 to react with carbon and iron and form their respective oxides. Both reactions are strongly exothermic.
2. The reactor 702 may be heated electrically by inductive coupling with an external source of electricity. Electricity can be generated from process steam raised by cooling the exit gases from reactor 702. Other means of electrical heating are possible, such as plasma torch heating.
3. The molten metal and slag in reactor 702 may be superheated during the prior stage regeneration of the reactive metal from the reactive metal oxide. Additional fuel (724 into reactor 704) is required. The sensible heat of the superheated mass of molten metal and slag that is available as the molten mass cools meets the endothermic requirement of the steam-carbon reaction.
4. Some portion of the steam-carbon reaction may be supplanted by supplying hydrogen and carbon monoxide derived from the volatile matter of the feedstock to the reactor 704. The reactions, which produce CO and $H_2$ from volatile matter, are not highly endothermic like the steam-carbon reaction. The requirement for CO and $H_2$ from the endothermic steam-carbon reaction is effectively reduced, as is the required heat.

As discussed in detail above, the addition of oxygen can adversely affect the economics of synthesis gas generation. Heating the reactor adds additional costs to the process. The preferred method of adding heat to the reactor 702 is to superheat the molten metal and add the volatile fraction of the feedstock of the reactor 704 to the reactor 702.

In accordance with the foregoing, the synthesis gas includes at least $H_2$ and CO. Other components can include $H_2O$, $CO_2$ and $CH_4$. It is generally preferred that the gas stream extracted from the reactor include at least about 50 vol. % $H_2$ and that the $CO_2$ content be not greater than about 15 vol. %, more preferably not greater than about 10 vol. %. In addition, the carbonaceous material, particularly coal, can include impurities that form acid gas components in the gas stream. Conventional approaches for removing the acid gas components such as hydrogen sulfide ($H_2S$), hydrogen chloride (HCl) and hydrogen fluoride (HF) may be used to clean the gas stream, if necessary. Alternatively, ammonia may be injected into the hot (400° C. to 500° C.) gas stream to react with the acid gas components producing, respectively, ammonium sulfide (($NH_4)_2S$), ammonium chloride ($NH_4Cl$) and ammonium fluoride ($NH_4F$). The ammonium salts that are produced may be removed from the gas stream, for example by pulsed ceramic filters. Thereafter, the purified gas stream can proceed directly to a conversion step, such as methanation, as is discussed below. If a slight excess of ammonia is left in the gas stream and the gas stream is converted to methane, the ammonia will burn when the methane is burned yielding water and nitrogen. The net heat of combustion for ammonia is 365 Btu/ft$^3$. By comparison, the net heat of combustion for CO is 322 Btu/ft$^3$.

The mixed ammonium salts formed according to the foregoing have a number of uses. They may be sold "as is," may be reprocessed to produce pure ammonium sulfate, an item of commerce, or may be employed in a "lime boil" to recover the ammonia for reuse and render the sulfur benign. In the lime boil process, lime (CaO) reacts with ammonium salts at or near the boiling temperature of water (e.g., about 80° C.) producing the corresponding calcium salt. For example:

$$CaO + (NH_4)_2S \rightarrow CaS + 2NH_3 + H_2O \qquad (13)$$

After recovery of the ammonia for reuse, air can be used to oxidize the calcium sulfide to calcium sulfate (gypsum), which can be used to produce wallboard or can be safely discarded.

Figure 8:
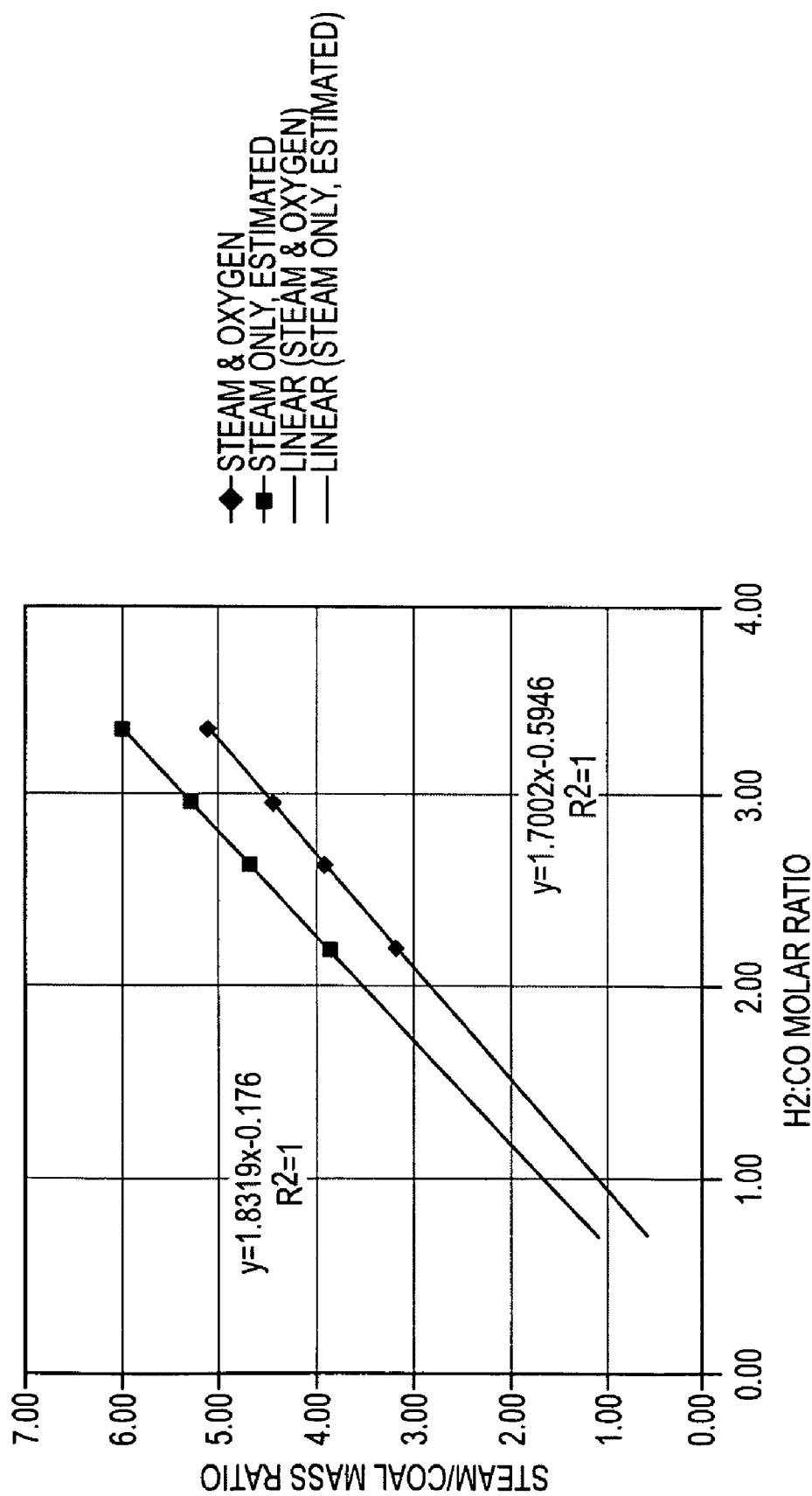
FIG. 8 illustrates the use of the steam/coal ratio to control the $H_2$:CO ratio according to an embodiment of the present invention.

The ratio of steam to coal fed to the reactor has a linear relationship with the $H_2$:CO ratio of the synthesis gas extracted from the reactor and can be used to control and adjust the $H_2$:CO ratio. The linear relationship between the ratio of steam to coal and $H_2$:CO of the present invention are illustrated in FIG. 8. A change of 6.06 percent in the ratio of steam to coal results in a 5 percent change in the $H_2$:CO ratio (for example, from 2.0 to 2.1). The steep slope (about 40 degrees) between these two linearly related parameters allows one ratio, the steam-carbon ratio, to be used to establish the other, the target $H_2$:CO ratio. According to one embodiment of the present invention, the mass ratio of steam to coal fed to the reactor is at least about 0.5:1, more preferably is at least about 1:1 and even more preferably is at least about 2:1.

It is a particular advantage of the present invention that the synthesis gas extracted from the reactor has a controlled molar ratio of hydrogen to carbon monoxide ($H_2$:CO) without requiring additional steps for the removal of carbon oxides to adjust the ratio prior to the synthesis of useful products such as methanol or methane. Accordingly, it is preferred that the molar ratio of $H_2$:CO in the gas stream extracted from the reactor is at least 1:1 and more preferably is at least about 1.5:1. In particular, the synthesis gas can be extracted from the reactor and provided to a methanol production step with a $H_2$:CO molar ratio of at least about 2:1 (theoretical stoichiometric requirement), more particularly about 2.1:1 (the preferred requirement established by practice). The synthesis gas provided to a methane production step can be controlled to have a $H_2$:CO molar ratio of at least about 3:1, the theoretical stoichiometric requirement. Thus, according to one embodiment, the gas stream extracted from the reactor has a $H_2$:CO molar ratio of from about 2:1 to 3:1.

After production of the synthesis gas, it can be converted to a hydrocarbon compound having either a gaseous, liquid or solid form. According to one preferred embodiment of the present invention, the synthesis gas is converted to methane. Methods for converting synthesis gas to methane are known to those skilled in the art. Typically, the synthesis gas is contacted with a catalyst at an elevated temperature. The catalysts can be, for example, nickel or molybdenum based catalysts supported on a carrier such as alumina. Examples of methanation catalysts and reaction conditions are illustrated in U.S. Pat. No. 4,540,714 by Pedersen et al., U.S. Pat. No. 4,525,482 by Ohaski et al. and U.S. Pat. No. 4,130,575 by Jrn. Each of the foregoing U.S. patents is incorporated herein by reference in its entirety.

The methane formed from the synthesis gas can be burned directly in a combined cycle generator to produce electricity. Although the synthesis gas can be burned directly, it is generally more economical to convert the synthesis gas to methane.

Methods of converting synthesis gas to methanol are known in the art and involve the contact of the synthesis gas, under pressure, with catalysts such as copper/zinc/chromium oxide. Examples of processes for converting synthesis gas to methanol and other alcohols are disclosed in U.S. Pat. No. 4,348,487 by Goldstein et al., U.S. Pat. No. 4,843,101 by Klier et al, U.S. Pat. No. 5,703,133 by Vanderspurt et al., and U.S. Pat. No. 6,248,796 by Jackson et al., which are incorporated herein by reference in their entirety. Synthesis gas can also be converted to synthetic crude using known Fischer-Tropsch processes.

To conserve heat it may be desirable to keep the synthesis gas stream exiting baghouse at its elevated temperature (400° C. to 500° C.) prior to its being converted into methanol or methane. To do so, anhydrous ammonia may be injected into the gas stream to react with the acid gas components producing ammonium sulfide ($(NH_4)_2S$), ammonium chloride ($NH_4Cl$) and ammonium fluoride ($NH_4F$). The ammonium salts that are produced may be removed from the gas stream, for example by pulsed ceramic filters. Thereafter, the purified gas stream can proceed directly to a conversion step without significant reheating.

In accordance with an alternative embodiment of the present invention, a precursor gas composition can be formed in a reactor that can be converted to ammonia ($NH_4$). According to this embodiment, steam introduced into a reactor containing a reactive metal to form hydrogen, substantially as is described above. In addition, air or another gas containing nitrogen and oxygen is introduced into the reactor such that the gas extracted from the reactor has a molar ratio of $H_2$:$N_2$ of about 3:1 for the production of ammonia. The overall reaction is illustrated by Equation 14:

$$12H_2O+(4N_2+O_2)+14Fe \rightarrow 14FeO+12H_2+4N_2 \qquad (14)$$

Control over the ratio of steam to air that is input to the reactor can be used to control the ratio of hydrogen to nitrogen and so that the complete combustion of oxygen from air will provide sufficient heat for isothermally balancing the chemical (iron oxidation by steam) and environmental heat losses incurred in the reactor.

In a typical ammonia production method, a gas including hydrogen and nitrogen is compressed to about 200 atmospheres of pressure and passed over an iron catalyst at a temperature of from about 380° C. to about 450° C. The production of ammonia from hydrogen and nitrogen is illustrated in: U.S. Pat. No. 4,600,571 by McCarroll et al.; U.S. Pat. No. 4,298,588 by Pinto; and U.S. Pat. No. 4,088,740 by Gaines. Each of the foregoing U.S. patents is incorporated herein by reference in their entirety.

The resulting ammonia can be used in a number of applications. For example, the ammonia can be converted to urea for use in fertilizers. The ammonia can also be used to reduce $NO_x$ emissions from coal-fired power plants and for the manufacture of various ammonium-containing compounds.

It is particularly noteworthy in accordance with the foregoing description that essentially the same plant equipment can be utilized to produce different gas streams (e.g., hydrogen gas, sythesis gas or an ammonia precursor gas) by simply changing the reactants that are admitted to the reactor that is converting the reactive metal to a metal oxide. Thus, a single plant can readily produce a variety of valuable gas streams and the type of gas stream can be switched rapidly.

EXAMPLES

Example 1

In this Example 1, a synthesis gas with a target molar $H_2$:CO ratio of about 2:1 was produced. This is the $H_2$:CO ratio that is required to make methanol.

A reactor was fabricated using an alumina closed-ended tube (2" ID×19" long) placed inside a stainless steel, closed-ended three-inch diameter pipe. The open end of the pipe was sealed with a flange. A one-inch exhaust line was provided to carry the synthesis gas from the reactor through a port on the flange. After exiting the reactor, the synthesis gas proceeded through a water-chilled condenser. Immediately after exiting the condenser, the synthesis gas was sampled using TEDLAR bags. The synthesis gas proceeded through an ice-chilled condenser, where it was scrubbed of particulates. Finally, the synthesis gas entered a floating drum, where the volumetric flow was measured.

A ½" OD stainless steel lance was inserted through a second port in the flange and extended into the reactor. A flow of either steam or inert gas could be injected into the reactor through the lance. Coal was injected into the steam flow, thereby using the steam to carry the coal into the reactor.

The reactor was charged with 0.7 kg of tin metal and 0.7 kg of iron powder and heated to 1200° C. Ten grams of coal were loaded into a series of valves attached to the lance and adapted to inject the coal into the steam flow. A total of five individual charges of coal (2 grams each) were injected into the flow of steam. Analysis of the coal is shown in the Table 4 below.

TABLE 4

Coal Analysis

| Component | Percentage |
|---|---|
| Carbon | 74.48% |
| Hydrogen | 5.34% |
| Oxygen | 8.85% |
| Nitrogen | 1.31% |
| Sulfur | 1.95% |
| Ash | 8.07% |
| Total | 100.00% |

The total heating value of the coal was about 13,496 Btu/lb. The heated reactor was purged using a flow of helium through the lance at 1.25 standard liters/minute (slpm). The lance was not in contact with the molten bath at this time. Helium flow was terminated, the lance was inserted in the molten bath, and steam was injected through the lance into the molten bath at 7.5 slpm. Hydrogen gas was produced for four minutes by the reaction of steam oxidizing iron in the bath.

After four minutes, coal was injected into the steam lance, thereby injecting both coal and steam into the molten bath. The coal was injected at 1.33 g/min by injecting 2 grams of coal into the steam line every 1.5 minutes. In off-reactor tests, the coal was observed to continuously eject from the bottom of the lance during this 1.5-minute time frame at the steam rate used in this experiment.

Fifteen to thirty seconds after each injection, a ½ liter synthesis gas sample was taken using a TEDLAR bag and the sample was analyzed using gas chromatography at a later time. The average gas composition is shown below in Table 5.

TABLE 5

Synthesis Gas Composition

| Synthesis Gas Component | Average Composition (vol. %) |
|---|---|
| Hydrogen | 60.2 |
| Carbon Monoxide | 26.5 |
| Carbon Dioxide | 11.2 |
| Methane | 2.1 |
| Total | 100.0 |

The $H_2$:CO molar ratio calculated from the above data is 2.27:1, slightly above the 2:1 target. The flow of synthesis gas from the reactor was 4.75 liters/minute, calculated by measuring the change in gas volume in the exhaust collection drum over time.

Example 2

10 grams of coal were injected with steam into a molten tin-iron bath (50 wt. % tin and 50 wt. % iron) having a temperature of 1200° C. The steam flow rate was 1.5 lbs/hr (14 l/min at standard conditions, 70 l/min at tubing) and the coal was injected in 2 gram charges, 5 charges total (10 grams) at a rate of 1 charge every 1-2 minutes.

After injecting steam for 7 minutes into the molten metal (to stabilize $H_2$ production), coal was fed into the reactor in 2-gram charges. The coal and steam were then injected into the molten metal through the lance. A new charge of coal was fed into the line every 1.5 to 2 minutes. In this manner, from the initial charge, 10 grams of coal were fed into the reactor over 6.5 minutes. Gas chromatograph samples were taken of the exhaust gas flow 10 to 30 seconds after each charge was injected. On average, a gas flow of 6.7 liters/min was obtained. Previously, a blank run of 1.5 lb/hr of steam by itself through the process created 2.2 liters/min of hydrogen (no tin, iron or coal in the process). Therefore, it was calculated that 4.5 liter/min of gas was produced from the reactions of the steam and coal in the tin/iron melt.

Of the 4.5 liter/min of gas, the average gas composition was measured and the results are illustrated in Table 6.

TABLE 6

Synthesis Gas Composition

| Gas Component | Quantity (vol. %) |
|---|---|
| $H_2$ | 66.2 |
| CO | 18.1 |
| $CH_4$ | 3.5 |
| $CO_2$ | 12.1 |

As is illustrated in Table 6, the gas composition had an average $H_2$:CO molar ratio of 3.66:1.

If the data from Example 1 and Example 2 are extrapolated, it is possible to project that a steam flow requirement of about 6.24 standard liters/min is necessary to produce a 2:1 ($H_2$:CO) ratio for the production of methanol.

Example 3

The following Example 3 is an evaluation of a process for making syngas suitable for methanol synthesis that was performed using METSIM, a computer program for complex chemical, metallurgical and environmental processes available from Proware, Tucson, Ariz.

The carbonaceous material was coal from Ohio (Ohio #6, Carroll County, Ohio) with ASTM rank hvBb. The analysis of the coal is summarized in Table 7.

TABLE 7

Analysis of Ohio #6 Coal

| Proximate Analysis (%, As Received) | Moisture | 5.25 |
|---|---|---|
| | Volatile Matter | 37.19 |
| | Fixed Carbon | 48.19 |
| | Ash | 9.37 |
| | Total | 100.00 |
| Heating Value (Btu/lb As Received) | | 12,388 |
| Ultimate Analysis (%, Dry) | Carbon | 71.95 |
| | Hydrogen | 5.10 |
| | Oxygen | 7.77 |
| | Nitrogen | 1.43 |
| | Sulfur | 3.86 |
| | Chlorine | Not reported |
| | Fluorine | Not reported |
| | Phosphorous | Not reported |
| | Ash | 9.89 |
| | Total | 100.00 |
| Sulfur Forms (%, Dry) | Pyritic | 2.26 |
| | Sulfate | 0.12 |

TABLE 7-continued

Analysis of Ohio #6 Coal

| | |
|---|---|
| Organic | 1.48 |
| Total | 3.86 |

Figure 9:
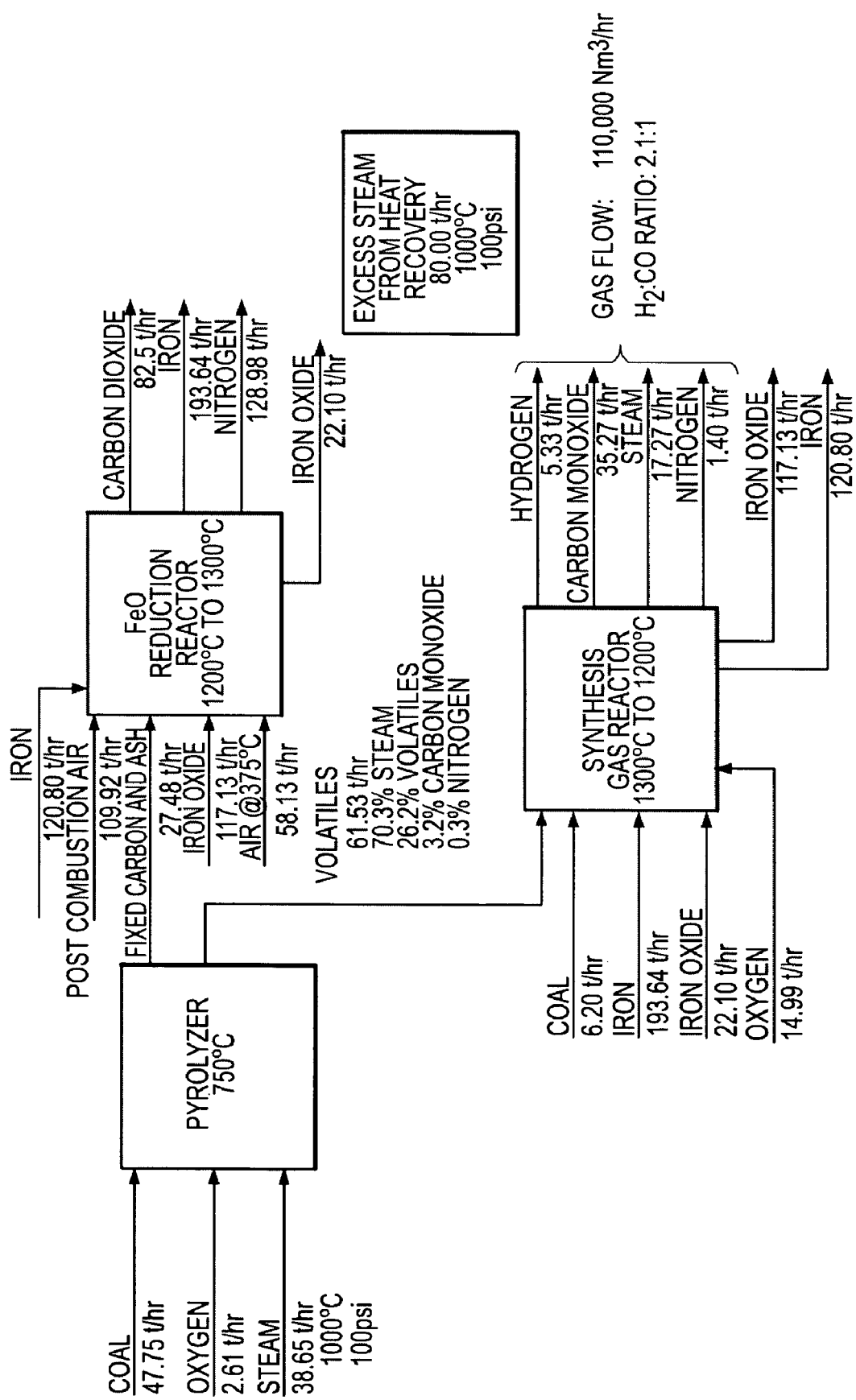
FIG. 9 illustrates a process flow for the production of a synthesis gas for methanol production according to an embodiment of the present invention.

FIG. 9 illustrates the material balance that can be achieved using iron as the reactive metal in the synthesis gas reactor at a temperature varying from 1200° C. to 1300° C. Specifically, the coal was fed to a pyrolyzer (750° C.) at a rate of 47.75 tons/hr with oxygen (2.61 tons/hr) and steam at 1000° C. (38.65 tons/hr). The volatiles, steam, CO and $N_2$ are transferred to the synthesis gas reactor and the fixed carbon and ash are transferred to the FeO reduction reactor. The resulting gas composition extracted from the synthesis gas reactor included hydrogen at 5.33 tons/hour and carbon monoxide at a rate of 35.27 tons/hr, for a $H_2$:CO molar ratio of about 2.1:1, which is ideal for conversion to methanol.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A method for the production of a gas stream comprising $H_2$ and CO comprising the steps of:
   a) providing a molten metal in a reactor comprising at least a first reactive metal;
   b) contacting steam with said molten metal to react a first portion of said steam with said reactive metal to form hydrogen gas and a metal oxide;
   c) contacting a carbonaceous material with said molten metal in the presence of steam to react said carbonaceous material with a second portion of said steam and form carbon monoxide gas; and
   d) extracting said gas stream from said reactor.

2. A method as recited in claim 1, wherein said reactive metal is iron.

3. A method as recited in claim 1, wherein said reactive metal is tin.

4. A method as recited in claim 1, wherein said gas stream extracted from said reactor comprises at least about 50 volume percent hydrogen gas.

5. A method as recited in claim 1, wherein said gas stream comprises not greater than about 15 vol. % carbon dioxide.

6. A method as recited in claim 1, wherein said gas stream comprises a molar $H_2$:CO ratio of at least about 1.5:1.

7. A method as recited in claim 1, wherein said gas stream comprises a molar $H_2$:CO ratio of at least about 2:1.

8. A method as recited in claim 1, wherein said gas stream comprises a molar $H_2$:CO ratio of from about 1:1 to about 3:1.

9. A method as recited in claim 1, further comprising the step of contacting an oxygen-containing gas with said molten metal.

10. A method as recited in claim 1, wherein said steps of contacting steam and contacting a carbonaceous material comprise the step of injecting said carbonaceous material entrained in said steam into said molten metal.

11. A method as recited in claim 1, further comprising the steps of:
   e) terminating said contacting of steam; and
   f) contacting said metal oxide with a reductant to reduce said metal oxide back to said molten metal.

12. A method as recited in claim 11, wherein said reductant comprises a particulate carbonaceous material.

13. A method as recited in claim 11, wherein said reductant comprises particulate coal.

14. A method as recited in claim 1, further comprising the step of adding a flux to said molten metal to promote the formation of a slag layer over said molten metal.

15. A method as recited in claim 1, wherein said carbonaceous material comprises a material selected from the group consisting of municipal waste, hazardous waste and petroleum coke.

16. A method as recited in claim 1, wherein said carbonaceous material comprises municipal waste.

17. A method as recited in claim 1, wherein the mass ratio of steam to carbonaceous material is at least about 0.5:1.

18. A method for the production of a gas stream comprising $H_2$ and CO comprising the steps of:
   a) providing a molten metal in a reactor comprising at least a first reactive metal, wherein said first reactive metal is iron;
   b) contacting steam with said molten metal to react a first portion of said steam with said reactive metal to form hydrogen gas and a metal oxide;
   c) contacting a carbonaceous material with said molten metal in the presence of steam to react said carbonaceous material with a second portion of said steam and form carbon monoxide gas;
   d) contacting an oxygen-containing gas with said molten metal to generate heat; and
   e) extracting said gas stream from said reactor.

* * * * *